US012765485B2

(12) United States Patent
Huijbregts-Doorduin et al.

(10) Patent No.: US 12,765,485 B2
(45) Date of Patent: Oct. 20, 2026

(54) **QTLS FOR MCLCV RESISTANCE IN *C. MELO***

(71) Applicant: RIJK ZWAAN ZAADTEELT EN ZAADHANDEL B.V., De Lier (NL)

(72) Inventors: Lena Johanna Huijbregts-Doorduin, De Lier (NL); Ram Kumar Basnet, De Lier (NL); Jasper Pieter Van Wijk, De Lier (NL); Zeger Otto Van Herwijnen, De Lier (NL); Paul De Graag, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 205 days.

(21) Appl. No.: 18/463,467

(22) Filed: Sep. 8, 2023

(65) Prior Publication Data

US 2024/0090420 A1 Mar. 21, 2024

Related U.S. Application Data

(63) Continuation-in-part of application No. PCT/EP2022/056545, filed on Mar. 14, 2022, which is a continuation-in-part of application No. PCT/EP2021/056386, filed on Mar. 12, 2021.

(30) Foreign Application Priority Data

Mar. 12, 2022 (WO) ................ PCT/EP2022/056545

(51) Int. Cl.

*A01H 6/34* (2018.01)
*A01H 1/00* (2006.01)
*A01H 1/04* (2006.01)
*A01H 5/10* (2018.01)

(52) U.S. Cl.

CPC ............... *A01H 6/344* (2018.05); *A01H 1/04* (2013.01); *A01H 1/126* (2021.01); *A01H 5/10* (2013.01)

(58) Field of Classification Search

None

See application file for complete search history.

(56) References Cited

FOREIGN PATENT DOCUMENTS

| | | | |
|---|---|---|---|
| WO | WO 2018/193044 | * | 10/2018 |
| WO | 2021/064118 A1 | | 4/2021 |

OTHER PUBLICATIONS

Saez et al. Plant Cell Rep (2017)36:1571-1584.*

J. K. Brown, et al., Phylogenetic analysis of Melon chlorotic leaf curl virus from Guatemala: Another emergent species in the Squash leaf curl virus clade, Virus Research (2011) 158:257-262.

Soon O. Park, et al., Detection of Loci for Cucurbit Yellow Stunting Disorder Virus Resistance in Cucumis melo L., Acta Horticulturae, Published by International Society For Horticultural Science, BE (2007) No. 763, 207-214.

Int'l Search Report and Written Opinion issued Jun. 14, 2022 in International Application No. PCT/EP2022/056545.

Ex parte Berg, Appeal 2022-003691, Decision on Appeal issued Oct. 14, 2022 in U.S. Appl. No. 13/336,477.

Ex parte Berg, Appeal 2024-002212, Decision on Appeal issued Oct. 21, 2024 in U.S. Appl. No. 18/054,639.

Ex parte C, 27 USPQ2d 1492 (BPAI 1992), 1992 WL 515817.

*Enzo Biochem, Inc.* v. *Gen-Probe Inc.,* 323 F.3d 956 (Fed. Cir. 2002).

Ex parte Kikuchi, Appeal No. 2006-3084, Decision on Appeal issued Mar. 16, 2007 in U.S. Appl. No. 10/673,860.

Ex parte Winner, Appeal 2020-000054, Decision on Appeal issued Apr. 16, 2020 in U.S. Appl. No. 14/931,601.

* cited by examiner

*Primary Examiner* — Medina A Ibrahim

(74) *Attorney, Agent, or Firm* — Duane Morris LLP; Thomas J. Kowalski

(57) ABSTRACT

The invention relates to a *Cucumis melo* plant that is resistant to MCLCV, which plant comprises a QTL on chromosome 11, and/or a QTL on chromosome 2, and/or a QTL on chromosome 6. The QTL is as comprised in the genome of a *Cucumis melo* plant representative seed of which was deposited with the NCIMB under deposit number NCIMB 43711, NCIMB 43712, NCIMB 43713, or NCIMB 43951.

20 Claims, 9 Drawing Sheets

Specification includes a Sequence Listing.

FIG. 1A

SEQ ID No. 1 - CM05672

TCCTCTAGCGATTCTGCAGATTGATCACATGCTCGTCTAGCATGGTGGTTGTCCCACTCATCTTCCAGC
ACCTTCTCCACCTCATCCGTCTGCTGTCTGTATYCATCGGTTAACAATTCGTTTTGGATGATCAGGTCATCATTAG
AGTTTGATTTCTCCACTGGCAATGCTGCAGATTCATCCGGTGCTCCTTGCTTCTCA

SEQ ID No. 2 - CM04510

AGTTGATGAATTTAAGATGAGGGTTGTTTACATTTTTGCAAATCCTCCGTCGCCTGTCCCAGAAGGAT
CTGAAGAAGGATCTCCTCCAAGGACCACTGGAATTGATGATGGAAACCAAAATTTTGCTTTATTTGATGCCGTA
AATGTCTTCCAARATTCTTTTCTAGATTTTTATTCTTATCCTCTCTTTTTTATCTATGA

SEQ ID No. 3 - CM04509

CCTTCTCGATTGCTGGGATAAAATTTGACGGAATAGCTTGTCCTACAATTATGTTCTCAAACTCAATT
TAGTTGTTGATCCTGGAGGAAGTGGTTCAATGTATCTGCCATTACAGATAAATAAAAGTGATGTTGAAACTACC
ACGTCACTACACCCAAAYAATACATAAGGATAGACAATGTAACTGTCATTGCAAACAG

SEQ ID No. 4 - CM05674

AGCCATTCTCAATGTAAGTAGAAACTAACTGAACAGAAAATCAGTACAATCGTTCTTATATTGGTTAC
CTCAGCACTAGCTCGGACGAAGCTACGAACAGCAATCCTCGAAGACAAGGGGTTCAAAGAAGTGGTGAGAGA
AGGAAAGTGCAAGGAACCCGATAGAAAACTGGAGGAGGACGGCAATCGAAGCATATGAAGC

SEQ ID No. 5 - CM05675

TGTATTCGAGAATTATCAACCACAAGAGTCAACAGATTGGGAGAGATCCCTTAATTCTGAAACTTATA
AGAGCCAATAACCTGAAAATTTAAATTTACCRCGAGCATCCTATAAAATAAAATGTGTAGAGACAAATATGGTC
CCAAAGTCAAATCATTGACAGTAGAAAAGATACATCTTCTGGTTAAAACATCAACGAAA

SEQ ID No. 6 - CM05667

ATTTAGGGGCCCACATAATTAACCGCACAAATGTCAGTGGGTGCACTCTTTCTCTTTTTAAATTGCGAC
TTTTCACATTCTAGCAACACAAGAATATCACTTGCCATAGTGCCACCAGTCTTCTTCACCAGCACCGAAGGTGA
GTCATGGATGAAATTCAAAGCCTCAAAAGGGTTTCAAGAGAAAGAGGTCTTTGAATCA

SEQ ID No. 7 - CM05668

TCTCTCCCTCTTCCACCTTTGTTACTCGCCGGAACGCCCCCACCTCTTATCTGTTGCATCCTAACGCTCTC
TTTTGCCGCCGTCCCTTCAACTCTTGTTCGCTCGCCATTTAGGTCTGTTCTCTTCTATCTTTTCTCTCTTCTTTTTTT
GTTTCATAGTGGCCTACGTTTGTAATGAACTTCATTTCTCAATTATAAATCT

SEQ ID No. 8 - CM05669

CAAAATTCAGATTATATTTGTAAATTTAATCAAAACTAAAACAGAGAAAACAGGTATCTTCAGCTCCTT
TACCGGTAACAAATCAAAATTAAGAATTCAAGAACATAACAGAAAACTTTAGAACTTCAATAAGT+AAATAAAC
AGAATCCTCAAAGTTAAGGCATTATACTTGTAAATTTAACCAAAACTAAAAACAGAAA

SEQ ID No. 9 - CM04507

TCATAATTCTCATCCTGGTTCTTTTCTGTAYCATATTGAAAGCGAGAGRGAAAACTGATTTTGATTTTG
GTCCATTTGGGCGTCTGTTTTAGATTGAAGACAGGGTTGAAAAGCTGCGGTCACTGGAGTGTTCTGTTATATCT
CCTCTGCAGTCTTTATATTCTTCTTCTCAAAGCATTGATGTTTGCTCAGGATCTTTAA

SEQ ID No. 10 - CM05670

AGAGGACTAAGAGGTCAAATATTCAAAYATTCTCCACTCTCGTATGTTGTGTGGAAACAAATGAAAGT
ATTAAAAGCGAATGCAAAATAGAAACACGTTTCAATGTTTATGGACATAATTGAAACTTTGAACTGCTTTTTCT
GTCAATCTAAATTTAATACCTTTGTACTTGCAAATTGCWATAATTTAAAGATTATGGGG

FIG. 1B

SEQ ID No. 11 - CM05916

TTTTGCTTTATGTATGACTTCTTATGCTACACYTGTATTTCAATGCATCTGAATTTTTGCAACACTTTAAT
GGCTCTTGTTCCTTCTTTTATGCRAAGCTAGATGTGGGATGTTCAGCTGGTCCCTAATATTCACACATGTTATTT
TGGTTTCTGTAATGCAGGTTGATGATGGTATTGTATTACCAGACAAAGCTTCTCT

SEQ ID No. 12 - CM05671

ATTTAAATTTGACTATAAATTTGCTTTATGGCTCAACAAACAAGAATATTGATAGGTTATAGAACGATT
TAGRGACTAGTTAGGCATCTTTTCAACCCATAAAAGCATATAAACATCACAATAACTTAAGTTTAATATCTAATA
TCTTGTGATTGTGGTATCTAGACATAAACTCGAGTCCATAAGACAAGGAAGAACTGT

SEQ ID No. 13 - CM06277

CATTACCTTTCTTTTCCCTATTTTCAGATCTTCATCATTTGGGTTTGTGTAACATCCTACATCTTTCCCTCC
CATCTCCTTCTTCAGCAATTCTAGATGTCTTCCCATATCTGTTTTCTCCGATTCTGCCATTTGGAGCTTCGATTTCA
GCTCGTTTATGTACGAAACGGCGTCACCGAGTAGTGAGGCTTTGTCCATTTT

SEQ ID No. 14 - CM00699

TTAAGCTACTTGAACTGGGATTTTCGGATCGGATTGGCTTTGCCGGAACGTTGCTGGAAGGGACGGT
GGTGGTAATTGAATCCTTCATCTCGATTGTACTCGATGGCTCACTGATCCACATCGACGACGGGTCGTTTTCCCC
TTCGTCTGCAGCGGATGCGGCGGCGGTAGTTCCCGAAATCCAAGAACTCGTCTCGAGAT

SEQ ID No. 15 - CM00219

ATTTATTTAAGGGAGCTGATTCGGATGGATACGCTACTTATTGCGAAATAGAAGTGCAGTTGGATTCT
GAATTTACTGCTGCAGCTGCAGCGATTTGTCGCTTGGGAGAAAATGAGTGTGTTTCCAGTAGCCAGCCTACAC
AGAGTTGTATAACTGAAAACCATAGACCTGAACCATCAGATCTTTCTCTCTCTTGTGAAG

SEQ ID No. 16 - CM06227

TTAAAMGACAGCAAAGAAGTGCCCGTAGAATGCAATTCTGACGTTGAAGACTTTCTTTCCTTTGCTGA
CAGCGTTCTGTGAAACAAACTTGTGTTTTCATACCTTCTTTGAGCCATGAAATTTTATACTTTTGGAGATAATTTC
TTTCCTCGCACGTATATAAGGATAACTATAGCTTATCTAATCTCATGACCAATTGGG

FIG. 2A

SEQ ID No. 17 - CM06865

GAATTTARGGTTAYGTGTARCCAATTGGTAYAATTGARAATAATAGAAACATYTTCYAGTAGAAGTTA
CAAATGACACAAAGAACCGAGTCATCTTTGGTCTGGTCTTGTTGTTAACCATCARTACCTTCAATACAGTGGRA
AAACCTTMGGYTTTTCTARCATAGCCAARTGTAAAGTGAGAGTTRACATATGTTAATTG

SEQ ID No. 18 - CM05138

AAAAYGGAAGTACACAGAGSCAKTGYCCNNNNCGCAATAGACAGTTGAACAAGCATGRAGAGARCA
CTAAAGRATATACCATRTAACTACCTGAGATTCAARACNNNNAGAAAGAAAACGGTGTCGGAATAGCATAGTT
TCCATAGAAAGAAACCATTTYCTCAAGTCCTCCCTRAGAYCAAGMCAAAATAATGATAAACA

SEQ ID No. 19 - CM06866

ARATAATTTTAAGAAAATATTGTGACAATTTGTAATTAAACATTATCYMTCGTGYAAYAAGRATGTTAT
TTTTGAGATTCATGAACAYGTATATGGTTATGAAATAAAAAATAAATTTAGAATTAAAATATTGTTTAGGATGT
CMMAAGTGCTAACTAATCAAGTTGTGATTTTGGTCCAAAATTYTGACTTTCTTRTTCY

SEQ ID No. 20 - CM06867

ATTTGTCCTACAAGCTTAAATYCTTGTCAAGKATCTAGTCCACTAATAAATGCTCCTGYYGYGACCTCTG
GAATTTTGCAGCAATCTGCAGGAACACCAATTGCATCACCAGTGGTTGCTGTGGTGAGTGATTGTTKATTATTT
CATAACACTTAAAGTTATGCACAATMTTTTCCCTTGCTCATCGTATGCATATCTGTC

SEQ ID No. 21 - CM06868

GCTYGTCAATCCAAGCACTTYCATCAAACAACGATTGCAGCAACTAAGCCCATTGCSTAGAGAAAAAA
CCACTTAGAGAAGAAGATTTACGATGACCCACAGCATCCTAATAAACGCCAATGCTCTTACAATATWTCTTTTT
GTATTCCATCTATCAGTAGTCCTTAACTAAGATCAAGGCACCATTTAAGCTAAACTTCA

SEQ ID No. 22 - CM06843

TATCCATGTGGGARACCTACATTATTATGCAAGGAGTTAGAAAGAACGAGCGACAGAAGACAATAGC
TAGTCAATTGCTTCAATTCAATTAGGATTCAAAGTTTTCATATTTTGTCARCTGGTGTAAGAACAGARGACTTAG
ACTTRCAATGAAGGATTTCCACTCTAGTCGTGTTTCCCCTTCTGTTGTCGTAGATGGCT

SEQ ID No. 23 - CM06844

AYGCYTATGGTCTCCAATAGACCAAAACAATAAGCATCAATGGCTTTCAMTTTAGAGTTTTGATTGGA
GAAGACAATAGTATATCCATCATCAATCTTTCAACAGAATCCAATACGTSAGTGCAAGAATTTTGGTTTCTACCA
ATCGTTTCTTYTRGCAACGTAAAAAAACATGGGTGAAGATRTGATRTGCCGACGTAAT

SEQ ID No. 24 - CM06845

ATGAAGTTTTCGTAGGACYGATARTTTTYYTTTGTRCATATTACTCYCATTCAACGTTTGRCAAGATATT
TGATATTAYAGCTATATTACGTAGTATTAGATATTTTCTCGTGCAAAATGCGYTTATTTGTGTAGTTCATTRAATT
GTTTAATCACAATTTACTAGTSAAAATGAGTATACCTCAACTCTCRTGATATTTG

SEQ ID No. 25 - CM06848

ATATGAGTATTACTTACTGTAGACCTGGTGGTTAACTCTGATCCACCGAAYTGCTGCTAACAATTGTTT
TATGGATTTGCTATCATCTTAAAKTGGTGAATTGGATGCTTGAATTGGAAGTARTTATGGCTATTTGTTTCAGGC
TTGTAAACGTGCTGGCTGGCTTCCACTYGAGGATAATAAGTATCCCAAARCAACCCA

SEQ ID No. 26 - CM06850

ATGTTTGAATACAATACAAATGTTCAWGAAAGTACAAAATATCATTATACWTTTTRCARAAGTGAATC
CAAAGTGATCMTAACGTGTTTCCTACTAGCAGTGTCTCAATCAATGTGTAGACAAGATAGCCATTTTGYAAAG
GCATCCTCTTWGTCAAAGTTATCAATCAAAGAAAATATGTTAGGGCCTYTCGGTGTCCA

FIG. 2B

SEQ ID No. 27 – CM06851

AAACCAAATGTATTARCCATAAAGTTAATTTTCAAAAAAATCTAAATGTATTSCCATTGTCCCGAGGGT
TYGTGTCATCTACTCTAACATACCAACTGATCTTAAGATAAAATGTATATTATATAAAATAACCACGTGATAGAA
ACATTTTCTTAGAACAACAAACCAATAATTAAGATAGTAAACACTAGCAAGTTCAAG

SEQ ID No. 28 - CM06853

CTTCTTTTTATTTRCCTATCTACCCTTYTTGTTTATGTTATTTTTAAAAGATGCATGCTTTACCATTGGTTT
ACATCTTTTATCTTGCAATATCATACTGGGAATCATGAGTTGCTTGTATTTCCTGGATGTGCAGGAAGCMRYAA
ACTCCRTAGTTAATRATCAAAAACTAGAGTTGCGTGGTCGGACRCTGAGGCTCTT

SEQ ID No. 29 - CM06854

TCCTTGACACCTAMATGTTGTAGTGTCAGGCGGTTGTYCCGTGAAATTAGTCRAGGTRCACRTAARCT
ARTYCAGACACTCACTAATATTGAATTAGCCAATCCTMAACTTTTTAGTRTAAGCATATRGCAAAATTCATCTCC
CTKAAGATAAGATCTTCAGTCTTCCATAGCAAACRGTGTAAAGATAAAACTTCACTT

SEQ ID No. 30 - CM06855

TGATCTCTTTGTATTWATATCAATGTCACAGATATCGTCAAGTTGGGAATGCAGTCGCGGTWTCGGT
GTCACGGGCATTGGGGTATTCCCTTGGATTGTCGGTGAGAAGAATGGGAGGTGATGAACCATTGATGGTTCTT
CCTCCCAAGTTCTCTCTTTCTAACTACATTCAATTACAAAAGCCACCTGATCATAATGATA

SEQ ID No. 31 - CM06856

ATAATTACATGACTTCRAACATCATTGTTTAAGTTMTTAGCTTTGTTGTGTTCTCAAAATGAYGATGTT
CACTTTGACATACGGTTCTAGTTTCTCAATGTGAGCGTAATTGAATTGGTACATGAMTTATAAAGTCAAATTCA
CACTCATGTTCAACTTAAAAATGTTTACCATTAAGAAAATATTATTTTAACKGTGTCA

SEQ ID No. 32 - CM06857

TTGGGCCAGAACTGGGAKGATGGATGTGAGGCTGAWACATAGCAGGAAGGGACAACAGATAAAAC
TACAGGTTCTATAGGTTCTATTTTGCACAACTGTATCCCCTTCCCTTGAATGAATAKGSTTTCCTTCTGAGGGCTT
GTCTTATCATCATTCACCTATCCATACATAWAAAAATAACTCCCCATACTAGCATCATCT

SEQ ID No. 33 - CM06858

TTTTTTATTTAGGGYYAARAGGGTWACRAGKATGTCGGAGAAAGTAGCCAATGGMRTGCTCTCTGGA
GTGRTTAAAGTTTCTGGATACTTTACAAGTTCAATGGCTAATTCAAAAGTTGGGAAGAAGTTTTTTGGAATGCT
TCCCGGGGAAATTGTACTAGCTTCYCTTGATGGATTTGGTATGTCAYCARCTCTAYTTTW

SEQ ID No. 34 - CM06859

CTGCCTGAGCCTGTGGAAAGAAAACAAACACTTACTGCTGAAAGGGTGAACATTCAATCCTGATSAAC
ATTATCTTTTGTATTTGGATGTATGTCTTCAAGGTTTGATGGATTTTTGTAGGTTCTTGGCATCYTGAAAAGAAT
AACTGATGAKGATTGYAAACTCTTGGGCCTCAATCCAAAGTATGCWCGRCCTGACTGG

SEQ ID No. 35 - CM06860

CCCAATATCCTCCATTAAAGCTTGGTAGGAAAACCATCTTTCAAAAATTTGAGGTTTCTTGACCAATTG
GTCTGTTTTGATTASTTCTCGGCAACCTTGTGTCAATCTTGGTTGTCTTGGATGTTTCTTGTTTTATCCATCATTTC
TACAACACTTGTTGATTTGTTGTGAGTTGATTCTCTTGGCGAGATATTTACCCAA

SEQ ID No. 36 - CM06861

ATTCTAAGGAAGAGACTTGAACTCTCTARTTGCACTATGTCACCCATTAGACCACATTAGACCACAAA
AGTTTGGACACTGACGCCACCTCTGAGACAACAAATAAAGGAAGGATATTGCAATGCGSGARGAGTTTCCACC
AACATTGCCTTCAATAAATACAATCRAAAAATAAATGTTGCAAGGTGTCCCYATCCTTCA

FIG. 3

| Score | Symptoms |
|---|---|
| 1 | No symptoms; |
| 2 | Some curling leaves, some yellowing; no fruit cracking |
| 3 | Severe curling and yellowing, and/or some fruit cracking |
| 4 | Severe curling and yellowing; severe fruit cracking |

FIG. 4

| Accession/SSD line | Score |
|---|---|
| Caribbean Gold | 4.0 |
| GBN.08.32-27 | 1.0 |
| Vedrantais | 4.0 |
| (GBN.08.32-27 x Vedr)_3 | 1.0 |
| (GBN.08.32-27 x Vedr)_8 | 1.5 |
| (GBN.08.32-27 x Vedr)_12 | 2.5 |
| (GBN.08.32-27 x Vedr)_19 | 1.0 |
| (GBN.08.32-27 x Vedr)_21 | 1.5 |
| (GBN.08.32-27 x Vedr)_23 | 1.0 |
| (GBN.08.32-27 x Vedr)_24 | segr |
| (GBN.08.32-27 x Vedr)_28 | 1.5 |
| (GBN.08.32-27 x Vedr)_31 | 1.0 |
| (GBN.08.32-27 x Vedr)_32 | 3.0 |
| (GBN.08.32-27 x Vedr)_42 | 1.0 |
| (GBN.08.32-27 x Vedr)_43 | 3.5 |
| (GBN.08.32-27 x Vedr)_45 | segr |
| (GBN.08.32-27 x Vedr)_48 | 2.5 |
| (GBN.08.32-27 x Vedr)_49 | 1.0 |
| (GBN.08.32-27 x Vedr)_50 | 4.0 |
| (GBN.08.32-27 x Vedr)_52 | 4.0 |
| GBN.08.32-27 | 1.0 |
| Vedrantais | 4.0 |
| (GBN.08.32-27 x Vedr)_65 | 1.0 |
| (GBN.08.32-27 x Vedr)_70 | 1.0 |
| (GBN.08.32-27 x Vedr)_71 | na |
| (GBN.08.32-27 x Vedr)_77 | 1.0 |
| (GBN.08.32-27 x Vedr)_78 | 1.0 |
| (GBN.08.32-27 x Vedr)_88 | segr |
| (GBN.08.32-27 x Vedr)_93 | 1.0 |
| (GBN.08.32-27 x Vedr)_102 | 2.0 |
| (GBN.08.32-27 x Vedr)_104 | 1.5 |
| (GBN.08.32-27 x Vedr)_111 | 1.0 |
| (GBN.08.32-27 x Vedr)_118 | 1.0 |
| GBN.08.32-27 | 1.0 |
| Vedrantais | 4.0 |
| GBN.11251 | 1.0 |
| Vedrantais | 4.0 |
| (GBN.11251 x Vedr)_219 | 2.0 |
| (GBN.11251 x Vedr)_220 | 2.0 |
| (GBN.11251 x Vedr)_221 | 4.0 |
| (GBN.11251 x Vedr)_223 | 2.5 |
| (GBN.11251 x Vedr)_224 | 4.0 |
| (GBN.11251 x Vedr)_225 | 1.5 |
| (GBN.11251 x Vedr)_226 | 2.5 |

| Accession/SSD line | Score |
|---|---|
| (GBN.11251 x Vedr)_236 | 2.0 |
| (GBN.11251 x Vedr)_238 | 2.5 |
| (GBN.11251 x Vedr)_239 | 4.0 |
| (GBN.11251 x Vedr)_240 | 4.0 |
| (GBN.11251 x Vedr)_242 | 4.0 |
| (GBN.11251 x Vedr)_245 | 4.0 |
| (GBN.11251 x Vedr)_253 | 1.0 |
| (GBN.11251 x Vedr)_254 | 2.0 |
| (GBN.11251 x Vedr)_257 | 1.5 |
| (GBN.11251 x Vedr)_259 | 2.0 |
| (GBN.11251 x Vedr)_262 | 3.0 |
| (GBN.11251 x Vedr)_264 | 3.0 |
| (GBN.11251 x Vedr)_266 | 3.0 |
| (GBN.11251 x Vedr)_270 | 1.5 |
| (GBN.11251 x Vedr)_271 | 2.0 |
| (GBN.11251 x Vedr)_272 | 3.0 |
| GBN.11251 | 1.0 |
| (GBN.11251 x Vedr)_277 | 1.5 |
| (GBN.11251 x Vedr)_282 | 3.0 |
| (GBN.11251 x Vedr)_284 | 1.0 |
| (GBN.11251 x Vedr)_285 | 2.0 |
| (GBN.11251 x Vedr)_286 | 2.5 |
| (GBN.11251 x Vedr)_287 | 1.0 |
| (GBN.11251 x Vedr)_289 | 2.0 |
| (GBN.11251 x Vedr)_291 | 2.0 |
| (GBN.11251 x Vedr)_293 | 1.5 |
| (GBN.11251 x Vedr)_297 | 1.5 |
| (GBN.11251 x Vedr)_301 | 2.0 |
| (GBN.11251 x Vedr)_303 | 3.0 |
| (GBN.11251 x Vedr)_307 | 1.0 |
| (GBN.11251 x Vedr)_312 | 2.0 |
| (GBN.11251 x Vedr)_313 | 1.0 |
| (GBN.11251 x Vedr)_316 | 3.0 |
| (GBN.11251 x Vedr)_317 | 2.5 |
| (GBN.11251 x Vedr)_318 | 2.5 |
| (GBN.11251 x Vedr)_319 | 2.0 |
| (GBN.11251 x Vedr)_320 | 1.0 |
| (GBN.11251 x Vedr)_321 | 2.5 |
| (GBN.11251 x Vedr)_322 | 3.0 |
| (GBN.11251 x Vedr)_325 | 1.5 |
| (GBN.11251 x Vedr)_327 | 1.5 |
| GBN.11251 | 1.0 |
| Vedrantais | 4.0 |
| | |

FIG. 5

| Marker name | SEQ ID No. (Fig. 1) | QTL on chromosome | Position of the SNP in the SEQ of Fig. 1 | Nucleotide of the SNP in the sequence of Fig. 1, to be used as marker of the invention (resistant allele) | Nucleotide of the SNP in the wildtype (susceptible allele) | Physical position of the SNP on the public DHL92_v3.5 genome map (in bp) |
|---|---|---|---|---|---|---|
| CM05672 | **SEQ ID No. 1** | 11 | 101 | A | C | 28721781 |
| CM04510 | **SEQ ID No. 2** | 11 | 101 | A | G | 28857192 |
| CM04509 | **SEQ ID No. 3** | 11 | 101 | G | A | 29364282 |
| CM05674 | **SEQ ID No. 4** | 11 | 101 | C | A | 29923501 |
| CM05675 | **SEQ ID No. 5** | 11 | 101 | C | T | 31030314 |
| CM05667 | **SEQ ID No. 6** | 2 | 101 | T | C | 149156 |
| CM05668 | **SEQ ID No. 7** | 2 | 101 | G | A | 278557 |
| CM05669 | **SEQ ID No. 8** | 2 | 101 | G | A | 1173217 |
| CM04507 | **SEQ ID No. 9** | 2 | 101 | C | A | 1312791 |
| CM05670 | **SEQ ID No. 10** | 2 | 101 | C | T | 1340337 |
| CM05916 | **SEQ ID No. 11** | 2 | 101 | A | C | 1794949 |
| CM05671 | **SEQ ID No. 12** | 2 | 101 | A | G | 2409694 |
| CM06277 | **SEQ ID No. 13** | 6 | 101 | C | T | 34681025 |
| CM00699 | **SEQ ID No. 14** | 6 | 101 | C | A | 34681768 |
| CM00219 | **SEQ ID No. 15** | 6 | 101 | C | T | 34875376 |
| CM06227 | **SEQ ID No. 16** | 6 | 101 | A | C | 35936597 |

FIG. 6

| Control | plant_1 | plant_2 | plant_3 | plant_4 | Average |
|---|---|---|---|---|---|
| GBN.08.32-27 | 35.46 | 32.63 | 40.00 | 35.08 | **35.79** |
| GBN.08.32-27 | 34.57 | 35.07 | 32.74 | 33.38 | **33.94** |
| Vedrantais | 13.11 | 11.25 | 11.81 | 16.30 | **13.12** |
| Vedrantais | 13.08 | 13.42 | 13.12 | escape | **13.21** |

FIG. 7

| Marker name | SEQ ID No. (Fig. 2) | QTL on chromosome | Position of the SNP in the SEQ of Fig. 2 | Nucleotide of the SNP in the sequence of Fig. 2, to be used as marker of the invention (resistant allele) | Nucleotide of the SNP in the wildtype (susceptible allele) | Physical position of the SNP on the public DHL92_v3.5 genome map (in bp) |
|---|---|---|---|---|---|---|
| CM06865 | **SEQ ID No. 17** | 11 | 101 | C | A | 29681747 |
| CM05138 | **SEQ ID No. 18** | 11 | 101 | A | G | 29805004 |
| CM06866 | **SEQ ID No. 19** | 11 | 101 | G | A | 29878018 |
| CM06867 | **SEQ ID No. 20** | 11 | 101 | T | G | 30090856 |
| CM06868 | **SEQ ID No. 21** | 11 | 101 | A | G | 30489819 |
| CM06843 | **SEQ ID No. 22** | 2 | 101 | G | A | 382668 |
| CM06844 | **SEQ ID No. 23** | 2 | 101 | A | G | 533824 |
| CM06845 | **SEQ ID No. 24** | 2 | 101 | A | T | 961684 |
| CM06848 | **SEQ ID No. 25** | 2 | 101 | T | G | 1548824 |
| CM06850 | **SEQ ID No. 26** | 2 | 101 | G | A | 2007502 |
| CM06851 | **SEQ ID No. 27** | 2 | 101 | C | T | 2239143 |
| CM06853 | **SEQ ID No. 28** | 6 | 101 | G | A | 34785107 |
| CM06854 | **SEQ ID No. 29** | 6 | 101 | A | C | 34940136 |
| CM06855 | **SEQ ID No. 30** | 6 | 101 | G | A | 35059268 |
| CM06856 | **SEQ ID No. 31** | 6 | 101 | T | C | 35203339 |
| CM06857 | **SEQ ID No. 32** | 6 | 101 | T | G | 35299399 |
| CM06858 | **SEQ ID No. 33** | 6 | 101 | A | G | 35423369 |
| CM06859 | **SEQ ID No. 34** | 6 | 101 | G | A | 35545575 |
| CM06860 | **SEQ ID No. 35** | 6 | 101 | G | C | 35704399 |
| CM06861 | **SEQ ID No. 36** | 6 | 101 | A | T | 35819595 |

```
                              SEQUENCE LISTING


Sequence total quantity: 36
SEQ ID NO: 1            moltype = DNA  length = 201
FEATURE                 Location/Qualifiers
misc_feature            1..201
                        note = CM05672
source                  1..201
                        mol_type = genomic DNA
                        organism = Cucumis melo
SEQUENCE: 1
tcctctagcg attctgcaga ttgatcacat gctcgtctag catggtggtt gtcccactca  60
tcttccagca ccttctccac ctcatccgtc tgctgtctgt atycatcggt taacaattcg  120
ttttggatga tcaggtcatc attagagttt gatttctcca ctggcaatgc tgcagattca  180
tccggtgctc cttgcttctc a                                            201

SEQ ID NO: 2            moltype = DNA  length = 201
FEATURE                 Location/Qualifiers
misc_feature            1..201
                        note = CM04510
source                  1..201
                        mol_type = genomic DNA
                        organism = Cucumis melo
SEQUENCE: 2
agttgatgaa tttaagatga gggttgttta catttttgca aatcctccgt cgcctgtccc  60
agaaggatct gaagaaggat ctcctccaag gaccactgga attgatgatg gaaaccaaaa  120
ttttgcttta tttgatgccg taaatgtctt ccaarattct tttctagatt tttattctta  180
tcctctcttt tttatctatg a                                            201

SEQ ID NO: 3            moltype = DNA  length = 201
FEATURE                 Location/Qualifiers
misc_feature            1..201
                        note = CM04509
source                  1..201
                        mol_type = genomic DNA
                        organism = Cucumis melo
SEQUENCE: 3
ccttctcgat tgctgggata aaatttgacg gaatagcttg tcctacaatt atgttctcaa  60
actcaaattt agttgttgat cctggaggaa gtggttcaat gtatctgcca ttacagataa  120
ataaaagtga tgttgaaact accacgtcac tacacccaaa yaatacataa ggatagacaa  180
tgtaactgtc attgcaaaca g                                            201

SEQ ID NO: 4            moltype = DNA  length = 201
FEATURE                 Location/Qualifiers
misc_feature            1..201
                        note = CM05674
source                  1..201
                        mol_type = genomic DNA
                        organism = Cucumis melo
SEQUENCE: 4
agccattctc aatgtaagta gaaactaact gaacagaaaa tcagtacaat cgttcttata  60
ttggttacct cagcactagc tcggacgaag ctacgaacag caatcctcga agacaagggg  120
ttcaaagaag tggtgagaga aggaaagtgc aaggaacccg atagaaaact ggaggaggac  180
ggcaatcgaa gcatatgaag c                                            201

SEQ ID NO: 5            moltype = DNA  length = 201
FEATURE                 Location/Qualifiers
misc_feature            1..201
                        note = CM05675
```

```
source                  1..201
                        mol_type = genomic DNA
                        organism = Cucumis melo
SEQUENCE: 5
tgtattcgag aattatcaac cacaagagtc aacagattgg gagagatccc ttaattctga  60
aacttataag agccaataac ctgaaaattt aaatttaccr cgagcatcct ataaaataaa  120
atgtgtagag acaaatatgg tcccaaagtc aaatcattga cagtagaaaa gatacatctt  180
ctggttaaaa catcaacgaa a                                            201

SEQ ID NO: 6            moltype = DNA  length = 201
FEATURE                 Location/Qualifiers
misc_feature            1..201
                        note = CM05667
source                  1..201
                        mol_type = genomic DNA
                        organism = Cucumis melo
SEQUENCE: 6
atttaggggc ccacataatt aaccgcacaa atgtcagtgg gtgcactctt tctcttttta  60
aattgcgact tttcacattc tagcaacaca agaatatcac ttgccatagt gccaccagtc  120
ttcttcacca gcaccgaagg tgagtcatgg atgaaattca aagcctcaaa agggtttcaa  180
gagaaagagg tctttgaatc a                                            201

SEQ ID NO: 7            moltype = DNA  length = 201
FEATURE                 Location/Qualifiers
misc_feature            1..201
                        note = CM05668
source                  1..201
                        mol_type = genomic DNA
                        organism = Cucumis melo
SEQUENCE: 7
tctctccctc ttccaccttt gttactcgcc ggaacgcccc cacctcttat ctgttgcatc  60
ctaacgctct cttttgccgc cgtcccttca actcttgttc gctcgccatt taggtctgtt  120
ctcttctatc ttttctctct tcttttttg tttcatagtg gcctacgttt gtaatgaact  180
tcatttctca attataaatc t                                            201

SEQ ID NO: 8            moltype = DNA  length = 201
FEATURE                 Location/Qualifiers
misc_feature            1..201
                        note = CM05669
misc_feature            135
                        note = /note="n= a or c or t or g"
source                  1..201
                        mol_type = genomic DNA
                        organism = Cucumis melo
SEQUENCE: 8
caaaattcag attatatttg taaatttaat caaaactaaa acagagaaaa caggtatctt  60
cagctccttt accggtaaca aatcaaaatt aagaattcaa gaacataaca gaaaacttta  120
gaacttcaat aagtnaaata aacagaatcc tcaaagttaa ggcattatac ttgtaaattt  180
aaccaaaact aaaaacagaa a                                            201

SEQ ID NO: 9            moltype = DNA  length = 201
FEATURE                 Location/Qualifiers
misc_feature            1..201
                        note = CM04507
source                  1..201
                        mol_type = genomic DNA
                        organism = Cucumis melo
SEQUENCE: 9
tcataattct catcctggtt cttttctgta ycatattgaa agcgagagrg aaaactgatt  60
ttgattttgg tccatttggg cgtctgtttt agattgaaga cagggttgaa aagctgcggt  120
cactggagtg ttctgttata tctcctctgc agtctttata ttcttcttct caaagcattg  180
atgtttgctc aggatcttta a                                            201

SEQ ID NO: 10           moltype = DNA  length = 201
FEATURE                 Location/Qualifiers
misc_feature            1..201
                        note = CM05670
source                  1..201
                        mol_type = genomic DNA
                        organism = Cucumis melo
SEQUENCE: 10
agaggactaa gaggtcaaat attcaaayat tctccactct cgtatgttgt gtggaaacaa  60
atgaaagtat taaaagcgaa tgcaaaatag aaacacgttt caatgtttat ggacataatt  120
gaaactttga actgcttttt ctgtcaatct aaatttaata cctttgtact tgcaaattgc  180
wataatttaa agattatggg g                                            201

SEQ ID NO: 11           moltype = DNA  length = 201
FEATURE                 Location/Qualifiers
misc_feature            1..201
```

```
                         note = CM05916
source                   1..201
                         mol_type = genomic DNA
                         organism = Cucumis melo
SEQUENCE: 11
ttttgcttta tgtatgactt cttatgctac acytgtattt caatgcatct gaatttttgc  60
aacactttaa tggctcttgt tccttctttt atgcraagct agatgtggga tgttcagctg  120
gtccctaata ttcacacatg ttattttggt ttctgtaatg caggttgatg atggtattgt  180
attaccagac aaagcttctc t                                            201

SEQ ID NO: 12            moltype = DNA  length = 201
FEATURE                  Location/Qualifiers
misc_feature             1..201
                         note = CM05671
source                   1..201
                         mol_type = genomic DNA
                         organism = Cucumis melo
SEQUENCE: 12
atttaaattt gactataaat ttgctttatg gctcaacaaa caagaatatt gataggttat  60
agaacgattt agrgactagt taggcatctt ttcaacccat aaaagcatat aaacatcaca  120
ataacttaag tttaatatct aatatcttgt gattgtggta tctagacata aactcgagtc  180
cataagacaa ggaagaactg t                                            201

SEQ ID NO: 13            moltype = DNA  length = 201
FEATURE                  Location/Qualifiers
misc_feature             1..201
                         note = CM06277
source                   1..201
                         mol_type = genomic DNA
                         organism = Cucumis melo
SEQUENCE: 13
cattaccttt cttttcccta ttttcagatc ttcatcattt gggtttgtgt aacatcctac  60
atctttccct cccatctcct tcttcagcaa ttctagatgt cttcccatat ctgttttctc  120
cgattctgcc atttggagct tcgatttcag ctcgtttatg tacgaaacgg cgtcaccgag  180
tagtgaggct ttgtccattt t                                            201

SEQ ID NO: 14            moltype = DNA  length = 201
FEATURE                  Location/Qualifiers
misc_feature             1..201
                         note = CM00699
source                   1..201
                         mol_type = genomic DNA
                         organism = Cucumis melo
SEQUENCE: 14
ttaagctact tgaactggga ttttcggatc ggattggctt tgccggaacg ttgctggaag  60
ggacggtggt ggtaattgaa tccttcatct cgattgtact cgatggctca ctgatccaca  120
tcgacgacgg gtcgttttcc ccttcgtctg cagcggatgc ggcggcggta gttcccgaaa  180
tccaagaact cgtctcgaga t                                            201

SEQ ID NO: 15            moltype = DNA  length = 201
FEATURE                  Location/Qualifiers
misc_feature             1..201
                         note = CM00219
source                   1..201
                         mol_type = genomic DNA
                         organism = Cucumis melo
SEQUENCE: 15
atttatttaa gggagctgat tcggatggat acgctactta ttgcgaaata gaagtgcagt  60
tggattctga atttactgct gcagctgcag cgatttgtcg cttgggagaa aatgagtgtg  120
tttccagtag ccagcctaca cagagttgta taactgaaaa ccatagacct gaaccatcag  180
atctttctct ctcttgtgaa g                                            201

SEQ ID NO: 16            moltype = DNA  length = 201
FEATURE                  Location/Qualifiers
misc_feature             1..201
                         note = CM06227
source                   1..201
                         mol_type = genomic DNA
                         organism = Cucumis melo
SEQUENCE: 16
ttaaamgaca gcaaagaagt gcccgtagaa tgcaattctg acgttgaaga ctttctttcc  60
tttgctgaca gcgttctgtg aaacaaactt gtgttttcat accttctttg agccatgaaa  120
ttttatactt ttggagataa tttctttcct cgcacgtata taaggataac tatagcttat  180
ctaatctcat gaccaattgg g                                            201

SEQ ID NO: 17            moltype = DNA  length = 201
FEATURE                  Location/Qualifiers
misc_feature             1..201
                         note = CM06865
```

```
source                  1..201
                        mol_type = genomic DNA
                        organism = Cucumis melo
SEQUENCE: 17
gaatttargg ttaygtgtar ccaattggta yaattgaraa taatagaaac atyttcyagt  60
agaagttaca aatgacacaa agaaccgagt catctttggt ctggtcttgt tgttaaccat  120
cartaccttc aatacagtgg raaaaccttm ggyttttcta rcatagccaa rtgtaaagtg  180
agagttraca tatgttaatt g                                            201

SEQ ID NO: 18           moltype = DNA  length = 201
FEATURE                 Location/Qualifiers
misc_feature            1..201
                        note = CM05138
misc_feature            29..32
                        note = /note="n = a or c or t or g"
misc_feature            105..108
                        note = /note="n = a or c or t or g"
source                  1..201
                        mol_type = genomic DNA
                        organism = Cucumis melo
SEQUENCE: 18
aaaayggaag tacacagags caktgyccnn nncgcaatag acagttgaac aagcatgrag  60
agarcactaa agratatacc atrtaactac ctgagattca aracnnnnag aaagaaaacg  120
gtgtcggaat agcatagttt ccatagaaag aaaccattty ctcaagtcct ccctragayc  180
aagmcaaaat aatgataaac a                                            201

SEQ ID NO: 19           moltype = DNA  length = 201
FEATURE                 Location/Qualifiers
misc_feature            1..201
                        note = CM06866
source                  1..201
                        mol_type = genomic DNA
                        organism = Cucumis melo
SEQUENCE: 19
arataatttt aagaaaatat tgtgacaatt tgtaattaaa cattatcymt cgtgyaayaa  60
gratgttatt tttgagattc atgaacaygt atatggttat gaaataaaaa ataaatttag  120
aattaaaata ttgtttagga tgtcmmaagt gctaactaat caagttgtga ttttggtcca  180
aaattytgac tttcttrttc y                                            201

SEQ ID NO: 20           moltype = DNA  length = 201
FEATURE                 Location/Qualifiers
misc_feature            1..201
                        note = CM06867
source                  1..201
                        mol_type = genomic DNA
                        organism = Cucumis melo
SEQUENCE: 20
atttgtccta caagcttaaa tycttgtcaa gkatctagtc cactaataaa tgctcctgyy  60
gygacctctg gaattttgca gcaatctgca ggaacaccaa ttgcatcacc agtggttgct  120
gtggtgagtg attgttkatt atttcataac acttaaagtt atgcacaatm ttttcccttg  180
ctcatcgtat gcatatctgt c                                            201

SEQ ID NO: 21           moltype = DNA  length = 201
FEATURE                 Location/Qualifiers
misc_feature            1..201
                        note = CM06868
source                  1..201
                        mol_type = genomic DNA
                        organism = Cucumis melo
SEQUENCE: 21
gctygtcaat ccaagcactt ycatcaaaca acgattgcag caactaagcc cattgcstag  60
agaaaaaacc acttagagaa gaagatttac gatgacccac agcatcctaa taaacgccaa  120
tgctcttaca atatwtcttt ttgtattcca tctatcagta gtccttaact aagatcaagg  180
caccatttaa gctaaacttc a                                            201

SEQ ID NO: 22           moltype = DNA  length = 201
FEATURE                 Location/Qualifiers
misc_feature            1..201
                        note = CM06843
source                  1..201
                        mol_type = genomic DNA
                        organism = Cucumis melo
SEQUENCE: 22
tatccatgtg ggaracctac attattatgc aaggagttag aaagaacgag cgacagaaga  60
caatagctag tcaattgctt caattcaatt aggattcaaa gttttcatat tttgtcarct  120
ggtgtaagaa cagargactt agacttrcaa tgaaggattt ccactctagt cgtgtttccc  180
cttctgttgt cgtagatggc t                                            201

SEQ ID NO: 23           moltype = DNA  length = 201
```

```
FEATURE                 Location/Qualifiers
misc_feature            1..201
                        note = CM06844
source                  1..201
                        mol_type = genomic DNA
                        organism = Cucumis melo
SEQUENCE: 23
aygcytatgg tctccaatag accaaaacaa taagcatcaa tggctttcam tttagagttt  60
tgattggaga agacaatagt atatccatca tcaatctttc aacagaatcc aatacgtsag  120
tgcaagaatt ttggtttcta ccaatcgttt cttytrgcaa cgtaaaaaaa catgggtgaa  180
gatrtgatrt gccgacgtaa t                                            201

SEQ ID NO: 24           moltype = DNA  length = 201
FEATURE                 Location/Qualifiers
misc_feature            1..201
                        note = CM06845
source                  1..201
                        mol_type = genomic DNA
                        organism = Cucumis melo
SEQUENCE: 24
atgaagtttt cgtaggacyg atarttttyy tttgtrcata ttactcycat tcaacgtttg  60
rcaagatatt tgatattaya gctatattac gtagtattag atattttctc gtgcaaaatg  120
cgyttatttg tgtagttcat traattgttt aatcacaatt tactagtsaa aatgagtata  180
cctcaactct crtgatattt g                                            201

SEQ ID NO: 25           moltype = DNA  length = 201
FEATURE                 Location/Qualifiers
misc_feature            1..201
                        note = CM06848
source                  1..201
                        mol_type = genomic DNA
                        organism = Cucumis melo
SEQUENCE: 25
atatgagtat tacttactgt agacctggtg gttaactctg atccaccgaa ytgctgctaa  60
caattgtttt atggatttgc tatcatctta aaktggtgaa ttggatgctt gaattggaag  120
tarttatggc tatttgtttc aggcttgtaa acgtgctggc tggcttccac tygaggataa  180
taagtatccc aaarcaaccc a                                            201

SEQ ID NO: 26           moltype = DNA  length = 200
FEATURE                 Location/Qualifiers
misc_feature            1..200
                        note = CM06850
source                  1..200
                        mol_type = genomic DNA
                        organism = Cucumis melo
SEQUENCE: 26
atgtttgaat acaatacaaa tgttcawgaa agtacaaaat atcattatac wttttrcara  60
agtgaatcca aagtgatcmt aacgtgtttc ctactagcag tgtctcaatc aatgtgtaga  120
caagatagcc attttgyaaa ggcatcctct twgtcaaagt tatcaatcaa agaaaatatg  180
ttagggccty tcggtgtcca                                              200

SEQ ID NO: 27           moltype = DNA  length = 201
FEATURE                 Location/Qualifiers
misc_feature            1..201
                        note = CM06851
source                  1..201
                        mol_type = genomic DNA
                        organism = Cucumis melo
SEQUENCE: 27
aaaccaaatg tattarccat aaagttaatt ttcaaaaaaa tctaaatgta ttsccattgt  60
cccgagggtt ygtgtcatct actctaacat accaactgat cttaagataa aatgtatatt  120
atataaaata accacgtgat agaaacattt tcttagaaca acaaaccaat aattaagata  180
gtaaacacta gcaagttcaa g                                            201

SEQ ID NO: 28           moltype = DNA  length = 201
FEATURE                 Location/Qualifiers
misc_feature            1..201
                        note = CM06853
source                  1..201
                        mol_type = genomic DNA
                        organism = Cucumis melo
SEQUENCE: 28
cttcttttta tttrcctatc taccccttytt gtttatgtta tttttaaaag atgcatgctt  60
taccattggt ttacatcttt tatcttgcaa tatcatactg ggaatcatga gttgcttgta  120
tttcctggat gtgcaggaag cmryaaactc crtagttaat ratcaaaaac tagagttgcg  180
tggtcggacr ctgaggctct t                                            201

SEQ ID NO: 29           moltype = DNA  length = 200
FEATURE                 Location/Qualifiers
```

```
misc_feature          1..200
                      note = CM06854
source                1..200
                      mol_type = genomic DNA
                      organism = Cucumis melo
SEQUENCE: 29
tccttgacac ctamatgttg tagtgtcagg cggttgtycc gtgaaattag tcraggtrca  60
crtaarctar tycagacact cactaatatt gaattagcca atcctmaact ttttagtrta  120
agcatatrgc aaaattcatc tccctkaaga taagatcttc agtcttccat agcaaacrgt  180
gtaaagataa aacttcactt                                              200

SEQ ID NO: 30         moltype = DNA  length = 201
FEATURE               Location/Qualifiers
misc_feature          1..201
                      note = CM06855
source                1..201
                      mol_type = genomic DNA
                      organism = Cucumis melo
SEQUENCE: 30
tgatctcttt gtattwatat caatgtcaca gatatcgtca agttgggaat gcagtcgcgg  60
twtcggtgtc acgggcattg gggtattccc ttggattgtc ggtgagaaga atgggaggtg  120
atgaaccatt gatggttctt cctcccaagt tctctctttc taactacatt caattacaaa  180
agccacctga tcataatgat a                                            201

SEQ ID NO: 31         moltype = DNA  length = 201
FEATURE               Location/Qualifiers
misc_feature          1..201
                      note = CM06856
source                1..201
                      mol_type = genomic DNA
                      organism = Cucumis melo
SEQUENCE: 31
ataattacat gacttcraac atcattgttt aagttmttag ctttgttgtg ttctcaaaat  60
gaygatgttc actttgacat acggttctag tttctcaatg tgagcgtaat tgaattggta  120
catgamttat aaagtcaaat tcacactcat gttcaactta aaaatgttta ccattaagaa  180
aatattattt taackgtgtc a                                            201

SEQ ID NO: 32         moltype = DNA  length = 201
FEATURE               Location/Qualifiers
misc_feature          1..201
                      note = CM06857
source                1..201
                      mol_type = genomic DNA
                      organism = Cucumis melo
SEQUENCE: 32
ttgggccaga actgggakga tggatgtgag gctgawacat agcaggaagg gacaacagat  60
aaaactacag gttctatagg ttctattttg cacaactgta tccccttccc ttgaatgaat  120
akgstttcct tctgagggct tgtcttatca tcattcacct atccatacat awaaaaataa  180
ctccccatac tagcatcatc t                                            201

SEQ ID NO: 33         moltype = DNA  length = 201
FEATURE               Location/Qualifiers
misc_feature          1..201
                      note = CM06858
source                1..201
                      mol_type = genomic DNA
                      organism = Cucumis melo
SEQUENCE: 33
tttttattt agggyyaara gggtwacrag katgtcggag aaagtagcca atggmrtgct  60
ctctggagtg rttaaagttt ctggatactt tacaagttca atggctaatt caaaagttgg  120
gaagaagttt tttggaatgc ttcccgggga aattgtacta gcttcycttg atggatttgg  180
tatgtcayca rctctayttt w                                            201

SEQ ID NO: 34         moltype = DNA  length = 201
FEATURE               Location/Qualifiers
misc_feature          1..201
                      note = CM06859
source                1..201
                      mol_type = genomic DNA
                      organism = Cucumis melo
SEQUENCE: 34
ctgcctgagc ctgtggaaag aaaacaaaca cttactgctg aaagggtgaa cattcaatcc  60
tgatsaacat tatcttttgt atttggatgt atgtcttcaa ggtttgatgg atttttgtag  120
gttcttggca tcytgaaaag aataactgat gakgattgya aactcttggg cctcaatcca  180
aagtatgcwc grcctgactg g                                            201

SEQ ID NO: 35         moltype = DNA  length = 201
FEATURE               Location/Qualifiers
misc_feature          1..201
```

-continued

```
                          note = CM06860
source                    1..201
                          mol_type = genomic DNA
                          organism = Cucumis melo
SEQUENCE: 35
cccaatatcc tccattaaag cttggtagga aaaccatctt tcaaaaattt gaggtttctt  60
gaccaattgg tctgttttga ttasttctcg gcaaccttgt gtcaatcttg gttgtcttgg  120
atgtttcttg ttttatccat catttctaca acacttgttg atttgttgtg agttgattct  180
cttggcgaga tatttaccca a                                            201

SEQ ID NO: 36             moltype = DNA  length = 201
FEATURE                   Location/Qualifiers
misc_feature              1..201
                          note = CM06861
source                    1..201
                          mol_type = genomic DNA
                          organism = Cucumis melo
SEQUENCE: 36
attctaagga agagacttga actctctart tgcactatgt cacccattag accacattag  60
accacaaaag tttggacact gacgccacct ctgagacaac aaataaagga aggatattgc  120
aatgcgsgar gagtttccac caacattgcc ttcaataaat acaatcraaa aataaatgtt  180
gcaaggtgtc ccyatccttc a                                            201
```

QTLS FOR MCLCV RESISTANCE IN *C. MELO*

RELATED APPLICATIONS AND INCORPORATION BY REFERENCE

This application is a continuation-in-part application of international patent application Serial No. PCT/EP2022/056545 filed 14 Mar. 2022, which published as PCT Publication No. WO 2022/189674 on 15 Sep. 2022, which claims benefit of international patent application Serial No. PCT/EP2021/056386 filed 12 Mar. 2021.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and can be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said XML copy, was created Sep. 1, 2023, is named Y7954-00582SL.xml and is 53,757 bytes in size.

FIELD OF THE INVENTION

The present invention relates to a melon (*Cucumis melo*) plant comprising a QTL that leads to Melon chlorotic leaf curl virus (MCLCV) resistance. The invention further relates to a methods involving a MCLCV resistant *Cucumis melo* plant as well as progeny, a seed, a fruit, a food product, a cell or tissue culture of MCLCV resistant *Cucumis melo* plant.

BACKGROUND OF THE INVENTION

Viral diseases pose one of the major threats vegetable growers encounter, both in protected and open field crop cultivation. Once a crop is infected, spread of the virus can occur rapidly through hard-to-control vectors, usually insects. In addition, cultivation methods often contribute to a further spread of the virus, by sap transmission through tools and fieldworkers.

The best protection against virus infection is the use of a resistant variety. Resistances against many known viruses have been identified, which resistances are incorporated in suitable melon varieties through breeding, allowing the growers to obtain a good yield even under virus pressure. Resistance to a certain virus will result in symptom reduction and allows a plant to produce fruits that have a good size, appearance and quality, even though the virus is not necessarily completely absent from the plant. Complete resistance restricts the replication of a virus in a host plant, resulting in a strong reduction or even absence of the virus in the plant.

A large and widespread group of viruses are classified in the genus of Begomoviruses, the major genus in the family of Geminiviruses. Begomoviruses are transmitted by whitefly vectors, usually *Bemisia tabaci* whiteflies. Since whiteflies are insects that are very hard to control, they affect many crops, and are abundantly present in many countries, an infection with Begomoviruses spread by whiteflies often results in major economic damage. Around the year 2000, severe virus symptoms were observed in large melon fields in Guatemala. Research determined that they were caused by a new Begomovirus species, which was named Melon chlorotic leaf curl virus (MCLCV) (Brown et al: *Melon chlorotic leaf curl virus, a new Begomovirus associated with Bemisia tabaci infestations in Guatemala*. Plant Dis. 85(9): 1027, 2001). Symptoms included foliar chlorosis and leaf curling, as well as fruit discoloration, cracking, and a reduced fruit set. The severe leaf curling and fruit cracking especially are the symptoms leading to devastating yield losses. In contrast to the already known, related, Squash leaf curl virus (SLCV), this new virus appeared to be very virulent in melon (*Cucumis melo*) and watermelon (*Citrullus lanatus*).

In the years following the first observation the virus was also found in other countries. The symptoms can have a considerable effect on the crop yield, but no resistance against MCLCV was identified in *Cucumis melo* so far.

Citation or identification of any document in this application is not an admission that such document is available as prior art to the present invention.

SUMMARY OF THE INVENTION

It is an object of the present invention to provide a cultivated melon plant of the species *Cucumis melo* that comprises one or more QTLs which confer resistance to Melon chlorotic leaf curl virus (MCLCV). Melon chlorotic leaf curl virus is abbreviated throughout this application as MCLCV.

The present invention relates to a melon (*Cucumis melo*) plant comprising a QTL that leads to Melon chlorotic leaf curl virus (MCLCV) resistance. The invention further relates to a methods involving the same as well as progeny, a seed, a fruit, a food product, a cell or tissue culture of the same. for producing such *Cucumis melo* plant and methods for identification and selection of such a plant comprising the QTL. The invention also relates to progeny, seed and fruit of the Melon chlorotic leaf curl virus resistant *Cucumis melo* plant, to propagation material suitable for producing the *Cucumis melo* plant, and to a food product comprising such melon fruit or part thereof. The invention further relates to a cell or a tissue culture that is produced from, or can be regenerated into, a Melon chlorotic leaf curl virus resistant *Cucumis melo* plant. The invention also relates to a marker for identification of a QTL that leads to Melon chlorotic leaf curl virus resistance in a *Cucumis melo* plant, and to use of said marker.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It can be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of melon *Cucumis melo* comprising one or more QTLs of the invention resulting in a MCLCV resistant plant were deposited with NCIMB Ltd, Wellshead Place, Dyce, Aberdeen, AB21 7 GB, UK, on 18 Jan. 2021. Seed of T 20R.XX 29250, comprising a QTL of the invention on chromosome 2 and on chromosome 6, was deposited under deposit accession number NCIMB 43711. Seed of T 20R.XX 29251, comprising a QTL of the invention on chromosome 2 and chromosome 11, was deposited under deposit accession number NCIMB 43712. Seed of T 20R.XX 29252, comprising a QTL of the invention on chromosome 2, chromosome 6, and chromosome 11, was deposited under deposit accession number NCIMB 43713. Seed of *Cucumis melo* T 20R.XX 29253, comprising a QTL of the invention on chromosome 6 and chromosome 11, was deposited under deposit accession number NCIMB 43951 with NCIMB Ltd, Wellshead Place, Dyce, Aberdeen, AB21 7 GB, UK on 14 Mar. 2022.

The Deposits with NCIMB Ltd, Wellshead Place, Dyce, Aberdeen, AB21 7 GB, UK, under deposit accession number NCIMB 43669 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary, including if the deposit ever becomes unviable during that period.

BRIEF DESCRIPTION OF THE DRAWINGS

The following detailed description, given by way of example, but not intended to limit the invention solely to the specific embodiments described, can best be understood in conjunction with the accompanying drawings.

FIGS. 1A-1B. Genomic sequences of SEQ ID NOS: 1-16 that can be used as markers, or can be used to develop markers, for the identification of a QTL of the invention. The SNP that indicates the resistant allele is present on position 101 of each sequence and is shown in bold and underlined.

FIGS. 2A-2B. Genomic sequences of SEQ ID NOS: 17-36 that can be used as markers, or can be used to develop markers, for the identification of a QTL of the invention. The SNP that indicates the resistant allele is present on position 101 of each sequence and is shown in bold and underlined.

FIG. 3. Scales MCLCV Resistance Scores.

FIG. 4. MCLCV Bio-Assay Results.

FIG. 5. QTL regions with linked SNP markers for QTL identification.

FIG. 6. qPCR values of resistant and susceptible controls.

FIG. 7. Additional markers to identify the presence of the QTLs.

DETAILED DESCRIPTION OF THE INVENTION

The present invention provides a cultivated *Cucumis melo* plant comprising a QTL on chromosome 11, and/or a QTL on chromosome 2, and/or a QTL on chromosome 6, which QTLs confer resistance to MCLCV.

In one embodiment the invention relates to a *C. melo* plant comprising a QTL on chromosome 11, or comprising a QTL on chromosome 2, or comprising a QTL on chromosome 6, which QTLs confer resistance to MCLCV.

In one embodiment, the invention relates to a cultivated *C. melo* plant comprising a QTL on chromosome 11 and a QTL on chromosome 2, or a QTL on chromosome 11 and a QTL on chromosome 6, or a QTL on chromosome 2 and a QTL on chromosome 6, or a QTL on chromosome 11 and a QTL on chromosome 2 and a QTL on chromosome 6, wherein the combination of QTLs confers resistance to MCLCV.

In one embodiment, the invention relates to a cultivated *C. melo* plant comprising at least two QTLs that confer resistance to MCLCV.

In a preferred embodiment, the invention relates to a cultivated *C. melo* plant comprising a QTL on chromosome 11 and a QTL on chromosome 6, wherein the combination of QTLs confers resistance to Melon chlorotic leaf curl virus (MCLCV).

In a preferred embodiment the invention relates to a cultivated *C. melo* plant comprising a QTL on chromosome 11 and a QTL on chromosome 2, wherein the combination of QTLs confers resistance to Melon chlorotic leaf curl virus (MCLCV).

In a preferred embodiment the invention relates to a cultivated *C. melo* plant comprising a QTL on chromosome 2 and a QTL on chromosome 6, wherein the combination of QTLs confers resistance to Melon chlorotic leaf curl virus (MCLCV).

In another preferred embodiment, the invention relates to a *C. melo* plant that is resistant to MCLCV and comprises at least a QTL on chromosome 6.

Within the species *C. melo* a huge amount of variation is present, which is manifested by a broad range of foliar and fruit characteristics. The species is therefore divided into many subspecies, many of whom are considered wild or non-cultivated. *C. melo* is thus in itself an extremely valuable source of genetic variation and a resource for breeding of many useful traits, including resistances. Although such traits are regularly found in crossable subspecies, the source itself is usually not directly considered to be suitable for agronomic cultivation. A large germplasm screen that included accessions from various non-cultivated *C. melo* subspecies was organized to get an insight in the presence of possible MCLCV resistant sources.

MCLCV is transmitted by an insect vector, more specifically by whiteflies, and mechanical transmission of the virus has so far been unsuccessful. Since bio-assays using whiteflies are quite complicated to perform in a controlled environment, bio-assays were carried out by doing screens in the open field in Guatemala. The presence of MCLCV in the field was confirmed by a qPCR test. After extensive screening including many cultivated and non-cultivated accessions, some accessions of non-cultivated *C. melo* subspecies were identified that were highly resistant to MCLCV (Example 1). It was also observed however that these accessions were sometimes segregating, and not all plants of an accession showed the resistance. A research program was subsequently set up to determine if the resistance could be maintained in uniform lines, if the resistance could be transferred to cultivated *Cucumis melo*, and to identify the genetics behind the resistance.

Crosses were made between resistant plants of the MCLCV resistant non-cultivated *C. melo* subspecies sources GBN.08.32 and GBN 11251, and the susceptible variety Vedrantais. This was followed by population development, through inbreeding and Single Seed Descent (SSD), for further disease testing and QTL mapping. F5 SSD populations were again observed in a field trial to confirm resistance, determine inheritance, and check for remaining variation. The identification and characterization of one or more QTLs that contribute to resistance gives the opportunity to use genetically linked markers to identify the presence of the QTL and thereby the presence of the resistance in many more populations and recombinant breeding lines, which is obviously much more efficient than the use of a bio-assay or qPCR analysis to confirm the resistance in each generation.

For this purpose QTL mapping studies were performed. A first QTL mapping study was done on F5 lines developed from both sources, and was based on symptom reduction. In this study, a QTL region on chromosome 11, and a QTL region on chromosome 2 were identified in one source, and in another source a QTL region on chromosome 6 was identified, which QTLs contributed to the symptom reduction (Example 2). In a second QTL mapping study, based on virus titer reduction in the plant, QTLs on chr 6 and chr 11 were found to be involved (Example 3). During further research a more detailed analysis of the QTL regions resulted in additional markers for identification of the presence of the QTLs (Example 5).

As used herein, the phrase "a QTL on chromosome 11, and/or a QTL on chromosome 2, and/or a QTL on chromosome 6" is to be read as a QTL of the invention on chromosome 11, or on chromosome 2, or on chromosome 6; or a QTL of the invention on chromosome 11 and chromosome 2; or a QTL of the invention on chromosome 11 and chromosome 6; or a QTL of the invention on chromosome 2 and chromosome 6; or a QTL of the invention on chromosome 11 and chromosome 2 and chromosome 6. A QTL of the invention is a QTL that confers resistance to Melon chlorotic leaf curl virus (MCLCV).

The QTL of the invention on chromosome 11 is located between SEQ ID NO: 1 and SEQ ID NO: 5. SEQ ID NOs: 1 and 5 are flanking the QTL region on chromosome 11. The SNP presented in any one of SEQ ID NO: 1 or 5 is a suitable genetically linked marker for identifying the presence of the QTL on chromosome 11. The QTL of the invention on chromosome 2 is located between SEQ ID NO: 6 and SEQ ID NO: 12. SEQ ID NOs: 6 and 12 are flanking the QTL region on chromosome 2. The SNP presented in any one of SEQ ID NO: 6 or 12 is a suitable genetically linked marker for identifying the presence of the QTL on chromosome 2. The QTL of the invention on chromosome 6 is located between SEQ ID NO: 13 and SEQ ID NO: 16. SEQ ID NOs: 13 and 16 are flanking the QTL region on chromosome 6. The SNP presented in any one of SEQ ID NO: 13 or 16 is a suitable genetically linked marker for identifying the presence of the QTL on chromosome 6.

In specific embodiments, the QTL on chromosome 11 is flanked by SEQ ID NO: 2 and SEQ ID NO: 5, or flanked by SEQ ID NO: 3 and SEQ ID NO: 5, or flanked by SEQ ID NO: 17 and SEQ ID NO: 5. In other embodiments, the QTL on chromosome 11 is flanked by SEQ ID NO: 2 and SEQ ID NO: 4, or flanked by SEQ ID NO: 2 and SEQ ID NO: 19, or flanked by SEQ ID NO: 2 and SEQ ID NO: 18. In a further embodiment, the QTL on chromosome 11 is flanked by SEQ ID NO: 17 and SEQ ID NO: 18.

In one embodiment, a cultivated *Cucumis melo* plant of the invention comprises a QTL on chromosome 11 between SEQ ID NO: 1 and SEQ ID NO: 5 which is genetically linked to a marker chosen from the group comprising the SNPs as presented in any one of SEQ ID NOs: 2 to 4 and SEQ ID NOs: 17 to 21, and/or a QTL on chromosome 2 between SEQ ID NO: 6 and SEQ ID NO: 12 which is genetically linked to a marker chosen from the group comprising the SNPs as presented in any one of SEQ ID NOs: 7 to 11 and SEQ ID NOs: 22 to 27, and/or a QTL on chromosome 6 between SEQ ID NO: 13 and SEQ ID NO: 16 which is genetically linked to a marker chosen from the group comprising the SNPs as presented in any one of SEQ ID NOs: 14 and 15 and SEQ ID NOs: 28 to 36. A genetically linked marker can be used for identification of the presence of a QTL, and comprises a marker represented by any one of the sequences listed in FIGS. 1A-1B and FIGS. 2A-2B that is present in the QTL.

A further marker for identification of the presence of a QTL of the invention can be based on any other polymorphism between a resistant plant of the invention and a susceptible control plant, wherein the polymorphism is located on chromosome 11 between SEQ ID NO: 1 and SEQ ID NO: 5, or on chromosome 2 between SEQ ID NO: 6 and SEQ ID NO: 12, or on chromosome 6 between SEQ ID NO: 13 and SEQ ID NO: 16.

FIGS. 1A-1B and FIGS. 2A-2B provide the sequences of the SEQ ID NOs: that can be used as markers, or used to develop markers, to identify the presence of a QTL of the invention leading to MCLCV resistance in a melon plant. FIG. 5 and FIG. 7 present the resistant marker allele, i.e. the nucleotide of the SNP in the sequence that identifies the presence of the QTL, and therefore a resistant plant, as well as the position of the SNP in the sequence of FIGS. 1A-1B. As used herein, the 'SNP presented in' a certain SEQ ID NO: is the nucleotide of the SNP within the sequence that is indicative of resistance, as given in the column 'Nucleotide of the SNP in FIGS. 1A-1B, to be used as marker of the invention' of FIG. 5, or in the column 'Nucleotide of the SNP in FIGS. 2A-2B, to be used as marker of the invention' of FIG. 7. This is alternatively called the resistant allele of the SNP marker. As used herein, the use of a certain SEQ ID NO: as a marker is the use of the resistant SNP presented in said SEQ ID NO: as a marker.

When the sequences of the markers are positioned on the publicly available genome reference sequence for *C. melo*, DHL92 v 3.5, the physical position to which the SNP polymorphism in said marker sequence corresponds can be derived. This position is also presented in FIG. 5 and FIG. 7. The public *C. melo* genome sequence DHL92 v 3.5 can for example be accessed at cucurbitgenomics.org and is the reference for 'the public melon genome' as used herein. The positions of the QTLs and the markers of the invention are derivable from the public genome, and these positions are relative to said physical positions.

Identifying the presence of a QTL by using a marker is in particular done by identifying the presence of the nucleotide at the position of the SNP that is indicative for the resistance. The wildtype nucleotide, alternatively called the susceptible allele of the SNP marker, is the nucleotide that is present on that position in the public genome.

As used herein, a *Cucumis melo* plant of the invention is a cultivated *C. melo* plant that is non-wild and has agronomical value. The *C. melo* plant of the invention is thus an agronomically elite plant. The sources in which the QTLs of the invention were identified were non-cultivated, non-agronomically elite material, categorized as *C. melo* subsp. *agrestis*. As used herein, non-cultivated, non-agronomically elite *C. melo* plants bear fruits with whitish green or whitish yellow flesh color, which fruits have an average brix that is lower than 8.0. The cultivated *C. melo* plant of the invention is not a plant of *C. melo* subsp. *agrestis*.

In one embodiment, the cultivated *C. melo* plant of the invention is a melon plant bearing fruits belonging to the Charentais, Cantaloupe, Honeydew, Galia, Piel de Sapo, Harper, Canary, Amarillo, *Ananas*, or Sprite type melon.

The cultivated *C. melo* plant of the invention bears sweet melon fruits with an average brix of 8.0 or higher.

As used herein, a marker is genetically linked to, and can therefore be used for the identification of a QTL of the invention, when the marker and the MCLCV resistance co-segregate in a segregating population resulting from a cross between a plant comprising a QTL of the invention and a plant lacking the QTL. A marker genetically linked to a QTL can be used for identification of that QTL because a linked marker is present in said QTL.

The presence of MCLCV resistance can be determined through a field assay. In a field assay, the plants that need to be tested are grown in an area that is known to have MCLCV infestation, for example in the Zacapa Valley in Guatemala. First, plants of a susceptible variety are sown, and after 2 weeks transplanted to the field. After transplanting they are covered in the field for 2 more weeks, after which the cover is removed. These plants are used for catching the virus, thereby creating a good source of virus concentration in the field. Plants to be tested, including a control variety, are sown 2 weeks later, also in trays, and transplanted to the field after 2 weeks. These plants are then also covered for 2 weeks. Observation of the MCLCV symptoms can start four or five weeks after uncovering the plants to be tested. Since MCLCV symptoms are clearly visible as fruit cracking, the best moment to do the field observation is when developed fruits are present.

MCLCV resistance is determined by comparison to a control variety known to be MCLCV susceptible. Examples of MCLCV susceptible melon varieties are Vedrantais and Caribbean Gold F1. Since no melon varieties that are resistant to MCLCV were known yet, it was not possible to include a resistant control before the present invention was done. However, as a resistant control a plant grown from seed deposited as NCIMB 43711, NCIMB 43712, or NCIMB 43713 can be used. A plant grown from seed deposited as NCIMB 43951 can also be used. Phenotypic resistance is suitably scored on a scale of 1-4; the scales of the scores can be found in FIG. 3. The field assay is performed properly when the susceptible controls have an average score that is 3.0 or higher than 3.0; when these symptoms are reached the assay is at the correct moment for scoring. To confirm that MCLCV is the cause of the symptoms, susceptible plants showing symptoms can be tested with PCR, using the primers and PCR program as described in Deng et al., 1994 (DENG D et al, *Detection and differentiation of whitefly-transmitted geminiviruses in plants and vector insects by the polymerase chain reaction with degenerate primers*; Ann. appl. Biol. (1994), 125, 327-336) to determine the presence of the MCLCV.

As used herein, a MCLCV resistant melon plant has an average score of 2.5 or lower than 2.5, preferably 2.0 or lower than 2.0, more preferably 1.5 or lower than 1.5, most preferably 1.0, when scoring according to FIG. 3 is used. Resistance can therefore alternatively be defined as the absence of fruit cracking under MCLCV incidence.

Reduction of virus replication can be measured by a qPCR test. To determine if a line has reduction or absence of MCLCV virus replication, the virus titer is determined in leaf samples that are taken from at least 5 plants of that line that are MCLCV infected. From each plant, two leaf punches of 6 mm in diameter are taken and subsequently ground in 100 µl of Lysis Buffer solution. This volume is used in a 96-well KingFisher Flex isolation protocol, whereby isolation of the DNA of the leaf material is done using the AGOWA DNA isolation kit (LGC Genomics). The samples are then analysed in a 96CFX qPCR thermocycler (Biorad) to get a Cq_MCLCV value, which represents the number of cycles needed to obtain the virus PCR product. The primers and PCR program that are used are as described in Deng et al., 1994 (supra).

In one embodiment, a resistant plant of the invention that comprises the QTL of the invention on chromosome 6 or comprises a QTL of the invention on chromosome 11 and chromosome 6 as defined herein, has an average Cq_MCLCV value that is in order of increased preference higher than 26.00, 27.00, 28.00, 29.00, 30.00, 31.00, 32.00, 33.00, 34.00, 35.00, 36.00, 37.00, 38.00, 39.00, or is 40.00. In a preferred embodiment the average Cq_MCLCV value is higher than 30.00. In a most preferred embodiment, the average Cq_MCLCV value is higher than 34.00. Calculation of an average value as described above is preferably an average taken from at least 2 trials.

A *C. melo* plant that has a QTL of the invention that leads to MCLCV resistance can be grown from seed deposited as NCIMB 43711, NCIMB 43712, NCIMB 43713, or NCIMB 43951.

NCIMB 43711 has the MCLCV resistance of the invention and comprises a QTL on chromosome 2 that can be identified in the deposit by SEQ ID NOs: 6 and 12, and a QTL on chromosome 6 that can be identified in the deposit by SEQ ID NOs: 13 and 16. Both QTLs are present in the deposit in homozygous form. The QTL on chromosome 2 can also be identified by determining the presence of at least one of the markers of the group comprising SEQ ID NOs: 7 to 11 and SEQ ID NOs: 22 to 27. The QTL on chromosome 6 can also be identified by determining the presence of at least one of the markers of the group comprising SEQ ID NOs: 14 and 15 and SEQ ID NOs: 28 to 36.

NCIMB 43712 has the MCLCV resistance of the invention and comprises a QTL on chromosome 11 that can be identified in the deposit by SEQ ID NOs: 1 and 5, and a QTL on chromosome 2 that can be identified in the deposit by SEQ ID NOs: 6 and 12. Both QTLs are present in the deposit in homozygous form. The QTL on chromosome 11 can also be identified by determining the presence of at least one of the markers of the group comprising SEQ ID NOs: 2 to 4 and SEQ ID NOs: 17 to 21. The QTL on chromosome 2 can also be identified by determining the presence of at least one of the markers of the group comprising SEQ ID NOs: 7 to 11 and SEQ ID NOs: 22 to 27.

NCIMB 43713 has the MCLCV resistance of the invention and comprises a QTL on chromosome 11 that can be identified in the deposit by SEQ ID NOs: 1 and 5; and a QTL on chromosome 2 that can be identified in the deposit by SEQ ID NOs: 6 and 12; and a QTL on chromosome 6 that can be identified in the deposit by SEQ ID NOs: 13 and 16. All QTLs are present in the deposit in homozygous form. The QTL on chromosome 11 can also be identified by determining the presence of at least one of the markers of a group comprising SEQ ID NOs: 2 to 4 and SEQ ID NOs: 17 to 21. The QTL on chromosome 2 can also be identified by determining the presence of at least one of the markers of a group comprising SEQ ID NOs: 7 to 11 and SEQ ID NOs: 22 to 27. The QTL on chromosome 6 can also be identified by determining the presence of at least one of the markers of a group comprising SEQ ID NOs: 14 and 15 and SEQ ID NOs: 28 to 36.

NCIMB 43951 has the MCLCV resistance of the invention and comprises a QTL on chromosome 11 that can be identified in the deposit by SEQ ID NOs: 1 and 5; and a QTL on chromosome 6 that can be identified in the deposit by SEQ ID NOs: 13 and 16. All QTLs are present in the deposit in homozygous form. The QTL on chromosome 11 can also be identified by determining the presence of at least one of the markers of a group comprising SEQ ID NOs: 2 to 4 and SEQ ID NOs: 17 to 21. The QTL on chromosome 6 can also be identified by determining the presence of at least one of the markers of a group comprising SEQ ID NOs: 14 and 15 and SEQ ID NOs: 28 to 36.

A plant comprising the QTL of the invention on chromosome 11, and/or the QTL of the invention on chromosome 2, and/or the QTL of the invention on chromosome 6, can be used as a resistant control variety in a MCLCV bioassay. When a plant, line, or population to be assessed shows the same level of resistance as NCIMB 43711, or NCIMB 43712, or NCIMB 43713, or NCIMB 43951 in a bio-assay, and this plant, line or population comprises a QTL as described herein on chromosome 11, and/or a QTL as described herein on chromosome 2, and/or a QTL as described herein on chromosome 6, this plant, line, or population is considered to have the MCLCV resistance of the invention and is therefore a plant of the invention.

The invention also relates to a melon fruit harvested from a plant of the invention, wherein the melon fruit comprises a QTL of the invention in its genome that leads to MCLCV resistance in the plant. This melon fruit is also referred to herein as ‘the fruit of the invention’ or ‘the melon fruit of the invention’. As used herein, ‘melon fruit’ comprises a fruit produced by a cultivated plant of the species *Cucumis melo.*

The present invention relates to a method for producing an MCLCV resistant *C. melo* plant comprising introducing a QTL on chromosome 11 that is flanked by SEQ ID NO: 1 and SEQ ID NO: 5, or that comprises at least one of SEQ ID NOs: 2 to 4, or at least one of SEQ ID NOs: 17 to 21, in a *C. melo* plant; and/or introducing a QTL on chromosome 2 that is flanked by SEQ ID NO: 6 and SEQ ID NO: 12, or that comprises at least one of SEQ ID NOs: 7 to 11, or at least one of SEQ ID NOs: 22 to 27, in a *C. melo* plant; and/or introducing a QTL on chromosome 6 that is flanked by SEQ ID NO: 13 and SEQ ID NO: 16, or that comprises at least one of SEQ ID NOs: 14 or 15, or at least one of SEQ ID NOs: 28 to 36, in a *C. melo* plant.

The present invention also relates to a method for producing an MCLCV resistant *C. melo* plant comprising introducing a QTL on chromosome 11 that is flanked by SEQ ID NO: 2 and SEQ ID NO: 5, or flanked by SEQ ID NO: 3 and SEQ ID NO: 5, or flanked by SEQ ID NO: 17 and SEQ ID NO: 5, or flanked by SEQ ID NO: 2 and SEQ ID NO: 4, or flanked by SEQ ID NO: 2 and SEQ ID NO: 19, or flanked by SEQ ID NO: 2 and SEQ ID NO: 18, or flanked by SEQ ID NO: 17 and SEQ ID NO: 18, in a *C. melo* plant.

A QTL of the invention can be introduced from another plant that comprises the QTL through commonly used breeding techniques, such as crossing and selection, when the plants are sexually compatible. Such introduction can be from a plant of the same species, that usually can be crossed easily, or from a plant of a related species. Difficulties in crossing can be overcome through techniques known in the art such as embryo rescue, or cisgenesis can be applied. Suitably markers as described herein are used to follow the incorporation of the QTL into another plant.

The above method can in particular be used to introduce a QTL of the invention into a plant species that is suitable for incorporation of such genetic information. In a particular embodiment, said QTL can be introduced from a *Cucumis melo* plant of a non-cultivated subspecies comprising the QTL, into a cultivated *Cucumis melo* plant lacking the QTL, for example by using standard breeding methods. In a particular embodiment, the non-cultivated subspecies comprising the QTL that is used as a source is a *C. melo* subsp. *agrestis*. In another embodiment said QTL can be introduced from a cultivated *Cucumis melo* plant comprising the QTL into another cultivated *Cucumis melo* plant lacking the QTL.

In one embodiment, the QTL on chromosome 11 can be introduced from a *Cucumis melo* plant representative seed of which was deposited with the NCIMB under deposit number NCIMB 43712, or NCIMB 43713, or NCIMB 43951, or from sexual or vegetative descendants thereof. Introduction of the QTL on chromosome 11 in *Cucumis melo* leads to increased MCLCV resistance.

In one embodiment, the QTL on chromosome 2 can be introduced from a *Cucumis melo* plant representative seed of which was deposited with the NCIMB under deposit number NCIMB 43711, or NCIMB 43712, or NCIMB 43713, or from sexual or vegetative descendants thereof. Introduction of the QTL on chromosome 2 in *Cucumis melo* leads to increased MCLCV resistance.

In one embodiment, the QTL on chromosome 6 can be introduced from a *Cucumis melo* plant representative seed of which was deposited with the NCIMB under deposit number NCIMB 43711, or NCIMB 43713, or NCIMB 43951, or from sexual or vegetative descendants thereof. Introduction of the QTL on chromosome 6 in *Cucumis melo* leads to increased MCLCV resistance.

Alternatively, a QTL of the invention can be transferred from another, sexually incompatible, plant, for example by using a transgenic approach. Techniques that can suitably be used comprise general plant transformation techniques known to the skilled person, such as the use of an *Agrobacterium*-mediated transformation method. Genome editing methods such as the use of a CRISPR/Cas system might also be employed to obtain a plant of the invention.

The invention further relates to a plant of the invention comprising a QTL of the invention leading to MCLCV resistance either homozygously or heterozygously. The plant is in particular a plant of an inbred line, a hybrid, a doubled haploid, or a plant of a segregating population. Preferably, the plant of the invention is a non-transgenic plant.

The invention also relates to a *Cucumis melo* seed comprising a QTL of the invention on chromosome 11, or on chromosome 2, or on chromosome 6, or a QTL of the invention on chromosome 11 and chromosome 2, or a QTL of the invention on chromosome 11 and chromosome 6, or a QTL of the invention on chromosome 2 and chromosome 6, or a QTL of the invention on chromosome 11 and chromosome 2 and chromosome 6, wherein the plant grown from the seed is a plant of the invention that is resistant to MCLCV. The invention also relates to seed produced by a plant of the invention. This seed harbors a QTL of the invention, and as such, a plant grown from said seed is a plant of the invention. The invention also relates to use of said seed for the production of a plant of the invention, by growing said seed into a plant.

The invention also relates to a plant part of a plant of the invention, such as a fruit or a seed, wherein the plant part comprises a QTL of the invention in its genome.

Moreover, the invention also relates to a food product or a processed food product comprising the melon fruit of the invention or part thereof. The food product can have undergone one or more processing steps. Such a processing step might comprise but is not limited to any one of the following treatments or combinations thereof: peeling, cutting, washing, juicing, cooking, cooling or a salad mixture comprising the fruit of the invention. The processed form that is obtained is also part of this invention.

The invention also relates to propagation material suitable for producing a *Cucumis melo* plant of the invention, wherein the propagation material is suitable for sexual reproduction, and is in particular selected from a microspore, pollen, an ovary, an ovule, an embryo sac, and an egg cell; or is suitable for vegetative reproduction, and is in particular selected from a cutting, a root, a stem, a cell, a protoplast; or is suitable for tissue culture of regenerable cells, and is in particular selected from a leaf, pollen, an embryo, a cotyledon, a hypocotyl, a meristematic cell, a root, a root tip, an anther, a flower, a seed, and a stem; wherein the plant produced from the propagation material comprises a QTL of the invention that confers MCLCV resistance.

The invention further relates to a cell comprising a QTL of the invention. A cell of the invention can be obtained from, or be present in, a plant of the invention. Such a cell can either be in isolated form, or a part of a complete plant, or from a part thereof, and still constitutes a cell of the invention because such a cell comprises the QTL as described herein, that leads to MCLCV resistance. Each cell of a plant of the invention carries the genetic information that leads to MCLCV resistance. A cell of the invention can also be a regenerable cell that can regenerate into a new plant of the invention. The presence of the genetic information in this context is the presence of a QTL on chromosome 11, and/or a QTL on chromosome 2, and/or a QTL on chromosome 6, wherein a QTL is as defined herein.

The invention further relates to plant tissue of a plant of the invention, which comprises a QTL on chromosome 11, and/or a QTL on chromosome 2, and/or a QTL on chromosome 6 as defined herein. The tissue can be undifferentiated tissue or already differentiated tissue. Undifferentiated tissue is for example a stem tip, an anther, a petal, pollen, and can be used in micropropagation to obtain new plantlets that are grown into new plants of the invention. The tissue can also be grown from a cell of the invention.

The invention moreover relates to progeny of a plant, a cell, a tissue, or a seed of the invention, which progeny comprises a QTL on chromosome 11, and/or a QTL on chromosome 2, and/or a QTL on chromosome 6 as defined herein, the presence of which QTL or combination of QTLs leads to MCLCV resistance. Such progeny can in itself be a plant, a cutting, a seed, a cell, or a tissue.

As used herein, progeny is intended to mean the first and all further descendants from a cross with a plant of the invention, wherein a cross comprises a cross with itself or a cross with another plant, and wherein a descendant that is determined to be progeny comprises a QTL of the invention. The plant of the invention that is used in this cross is optionally a plant grown from seed of deposit NCIMB 43711, NCIMB 43712, NCIMB 43713, or NCIMB 43951, or from progeny seed thereof which is a direct or further descendant through crossing a plant grown from the deposited seed with itself or with another plant for one or more subsequent generations, wherein the progeny seed has retained a QTL of the invention.

Progeny also encompasses a *C. melo* plant that carries a QTL on chromosome 11, and/or a QTL on chromosome 2, and/or a QTL on chromosome 6 as defined herein, which QTL confers increased MCLCV resistance, and is obtained from a plant, or progeny of a plant, of the invention by vegetative propagation or another form of multiplication.

The invention further relates to a part of a *C. melo* plant of the invention that is suitable for sexual reproduction, which plant part comprises a QTL on chromosome 11, and/or a QTL on chromosome 2, and/or a QTL on chromosome 6 in its genome, which QTL is as defined herein. Such a part is for example selected from the group consisting of a microspore, a pollen, an ovary, an ovule, an embryo sac, and an egg cell.

Additionally, the invention relates to a part of a *C. melo* plant of the invention that is suitable for vegetative reproduction, which is in particular a cutting, a root, a stem, a cell, or a protoplast that comprises a QTL on chromosome 11, and/or a QTL on chromosome 2, and/or a QTL on chromosome 6 in its genome, which QTL is as defined herein. A part of a plant as previously mentioned is considered propagation material. The plant that is produced from the propagation material comprises a QTL on chromosome 11, and/or a QTL on chromosome 2, and/or a QTL on chromosome 6 as defined herein, the presence of which QTL or combination of QTLs leads to MCLCV resistance.

The invention further relates to tissue culture of a plant of the invention, which is also propagation material and which comprises a QTL on chromosome 11, and/or a QTL on chromosome 2, and/or a QTL on chromosome 6 in its genome, which QTL is as defined herein. The tissue culture comprises regenerable cells. Such tissue culture can be selected or derived from any part of the plant, in particular from a leaf, pollen, an embryo, a cotyledon, a hypocotyl, a meristematic cell, a root, a root tip, an anther, a flower, a seed, or a stem. The tissue culture can be regenerated into a *C. melo* plant comprising a QTL on chromosome 11, and/or a QTL on chromosome 2, and/or a QTL on chromosome 6 as defined herein, wherein the regenerated *C. melo* plant comprises MCLCV resistance and is also part of the invention.

The invention additionally relates to the use of a plant of the invention in plant breeding. The invention thus also relates to a breeding method for the development of a cultivated *C. melo* plant that is resistant to MCLCV, wherein a plant comprising a QTL on chromosome 11, and/or a QTL on chromosome 2, and/or a QTL on chromosome 6 as defined herein is used for conferring said resistance to another plant. Seed being representative for a plant that can be used in plant breeding to develop another plant with MCLCV resistance was deposited with the NCIMB under accession numbers NCIMB 43711, NCIMB 43712, NCIMB 43713, and NCIMB 43951.

The invention also relates to the use of a QTL on chromosome 11, and/or a QTL on chromosome 2, and/or a QTL on chromosome 6 as defined herein for the development of a cultivated *Cucumis melo* plant that has resistance to MCLCV.

The invention also relates to a marker for the identification of MCLCV resistance in a *Cucumis melo* plant, which marker is any one of a group comprising SEQ ID NOs: 1, 5 and 2 to 4, and 17 to 21, for the identification of the QTL on chromosome 11; or any one of a group comprising SEQ ID NOs: 6, 12, and 7 to 11, and 22 to 27, for the identification of the QTL on chromosome 2; or any one of a group comprising SEQ ID NOs: 13, 16, and 14 and 15, and 28 to 36, for the identification of the QTL on chromosome 6. The use of any one of the SNP markers represented by SEQ ID NOs: 1 to 16 and SEQ ID NOs: 17 to 36 for identification of MCLCV resistance in a cultivated or non-cultivated *Cucumis melo* plant is also part of the invention. Any one of these markers can also be used to develop other markers in the respective QTL region for the identification of that QTL leading to MCLCV resistance, which use is also part of the present invention.

The present invention also relates to a method for selecting an MCLCV resistant *Cucumis melo* plant, comprising identifying the presence of a QTL on chromosome 11, and/or a QTL on chromosome 2, and/or a QTL on chromosome 6, which QTLs are as defined herein, and selecting a plant that comprises said QTL or combination of QTLs as an MCLCV resistant plant.

Identifying the presence of the QTL on chromosome 11 is suitably done using a marker, that is capable of identifying the SNP presented in any one of SEQ ID NOs: 1, 5, and 2 to 4, or the SNP presented in any one of SEQ ID NOs: 17 to 21. Identifying the presence of the QTL on chromosome 2 is suitably done using a marker, that is capable of identifying the SNP presented in any one of SEQ ID NOs: 6, 12, and 7 to 11, or the SNP presented in any one of SEQ ID NOs: 22 to 27. Identifying the presence of the QTL on chromosome 6 is suitably done using a marker, that is capable of identifying the SNP presented in any one of SEQ ID NOs: 13, 16, and 14 and 15, or the SNP presented in any one of SEQ ID NOs: 28 to 36. In one embodiment, the marker is the complete sequence of the SEQ ID NO:

The invention also relates to a method of assaying a *Cucumis melo* plant for the presence in its genome of a QTL on chromosome 11, and/or a QTL on chromosome 2, and/or a QTL on chromosome 6 conferring MCLCV resistance, comprising detecting the presence of at least one of a SNP marker presented in any one of SEQ ID NOs: 1 to 5, 17 to 21 for chromosome 11; SEQ ID NOs: 6 to 12, 22 to 27 for chromosome 2; and SEQ ID NOs: 13 to 16, 28 to 36 for chromosome 6, or any combination thereof, in the genome of the *Cucumis melo* plant. The plant to be assayed can either be a cultivated or a non-cultivated plant.

The method of assaying a *Cucumis melo* plant for the presence in its genome of a QTL on chromosome 11, and/or a QTL on chromosome 2, and/or a QTL on chromosome 6 conferring MCLCV resistance, optionally further comprises selecting a *Cucumis melo* plant that comprises said QTL or combination of QTLs as a MCLCV resistant plant. The *C. melo* plant that is thus selected can subsequently be used as a source for introgressing a MCLCV resistance QTL into a cultivated *C. melo* plant lacking that QTL.

The invention also relates to a method for the production of a *Cucumis melo* plant which is resistant to MCLCV, said method comprising:

crossing a plant of the invention, which comprises a QTL of the invention, with another plant;

optionally performing one or more rounds of selfing and/or crossing of the plant resulting from the cross to obtain a further generation population;

selecting from the plant resulting from the cross of step a), or from the further generation population of step b), a plant that comprises a QTL on chromosome 11, and/or a QTL on chromosome 2, and/or a QTL on chromosome 6 as defined herein.

The invention additionally provides a method for the production of a *Cucumis melo* plant which is resistant to MCLCV, comprising:

crossing a first *Cucumis melo* parent plant comprising a QTL of the invention with a second *Cucumis melo* parent plant that lacks said QTL;

backcrossing the plant resulting from step a) with the second parent plant for at least three generations;

selecting from the third or higher backcross population a plant that comprises at least the QTL of the invention of the first parent plant of step a).

The invention additionally provides for a method of introducing another desired trait into a *C. melo* plant comprising MCLCV resistance, comprising:

crossing a MCLCV resistant *C. melo* plant comprising a QTL of the invention with a second *C. melo* plant that comprises the other desired trait to produce F1 progeny;

optionally selecting in the F1 for a plant that comprises MCLCV resistance and the other desired trait;

crossing the, optionally selected, F1 progeny plant with either parent, to produce backcross progeny;

selecting backcross progeny comprising MCLCV resistance and the other desired trait; and optionally repeating steps c) and d) one or more times in succession to produce selected fourth or higher backcross progeny that comprises the other desired trait and has resistance to MCLCV.

Backcrossing is optionally done until the backcross progeny is stable and can be used as a parent line, which can be reached after 3 up to 10 backcrosses.

In one embodiment, the plant of the invention used in above-described methods is a plant grown from seed deposited under NCIMB accession number NCIMB 43711, NCIMB 43712, NCIMB 43713, or NCIMB 43951, or a progeny plant thereof that has retained a QTL of the invention.

Optionally, selfing steps are performed after any of the crossing or backcrossing steps in above-described methods. Selection of a plant comprising MCLCV resistance and the other desired trait can alternatively be done following any crossing or selfing step in the method. The other desired trait can be selected from, but is not limited to, the following group: resistance to bacterial, fungal or viral diseases, insect or pest resistance, improved germination, plant size, plant type, improved shelf-life, improved fruit quality, water stress tolerance, heat stress tolerance, and male sterility. The invention includes a *Cucumis melo* plant produced by this method and the *Cucumis melo* fruit obtained therefrom.

The invention further relates to a method for the production of a *Cucumis melo* plant comprising a QTL on chromosome 11, and/or a QTL on chromosome 2, and/or a QTL on chromosome 6, wherein the presence of said QTL or combination of QTLs leads to resistance to MCLCV, by using tissue culture or by using vegetative reproduction.

The invention further provides a method for the production of a *Cucumis melo* plant comprising a QTL of the invention and having resistance to MCLCV as defined herein by using a doubled haploid generation technique to generate a doubled haploid line, that homozygously comprises a QTL of the invention and is resistant against MCLCV.

The invention further relates to a method for the production of a cultivated *Cucumis melo* plant comprising a QTL on chromosome 11, and/or a QTL on chromosome 2, and/or a QTL on chromosome 6, wherein the presence of said QTL or combination of QTLs leads to MCLCV resistance, which method comprises growing a cultivated *Cucumis melo* seed comprising said QTL or combination of QTLs into the said *C. melo* plant. In one embodiment, the seed used in said method is seed deposited with the NCIMB under deposit number NCIMB 43711, NCIMB 43712, NCIMB 43713, or NCIMB 43951, or progeny seed thereof that has retained a QTL of the invention.

The invention further relates to a method for seed production comprising growing a *Cucumis melo* plant from a seed of the invention, allowing the plant to produce a fruit with seed, harvesting the fruit, and extracting those seed. Production of the seed is suitably done by selfing or by crossing with another plant that is optionally also a plant of the invention. The seed that is so produced has the capability to grow into a plant that is resistant to MCLCV. In a preferred embodiment in the plants used in seed production the QTL is homozygously present.

The invention further relates to hybrid seed and to a method for producing said hybrid seed, comprising crossing a first parent plant with a second parent plant and harvesting the resultant hybrid seed, wherein the first parent plant and/or the second parent plant is a plant of the invention comprising a QTL on chromosome 11, and/or a QTL on chromosome 2, and/or a QTL on chromosome 6, wherein the presence of said QTL or combination of QTLs leads to MCLCV resistance. The resulting hybrid seed and the plant that can be grown from the hybrid seed, comprising said QTL or combination of QTLs, which hybrid plant has resistance to MCLCV, is also a part of the invention. In a preferred embodiment, both parent plants comprise the QTL of the invention homozygously, and the hybrid seed therefore comprises the QTL of the invention homozygously.

Introgression of a QTL of the invention as used herein means introduction of a QTL from a donor plant comprising said QTL into a recipient plant not carrying said QTL by standard breeding techniques, wherein selection for plants comprising a QTL of the invention can be performed phenotypically by means of observation of the resistance to MCLCV, or selection can be performed with the use of a marker as defined herein, through marker assisted breeding, or a combination of these selection methods. Selection is started in the F1 or any further generation from an initial cross between the recipient plant and the donor plant, followed by either further crossing or selfing, suitably by using markers as identified and defined herein. The skilled person is familiar with creating and using new molecular markers that can be used to identify or are linked to a QTL of the invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Bio-Assay Through Field Screening for MCLCV Resistance

Because of increasing problems due to the presence of the new Begomovirus Melon Chlorotic Leaf Curl Virus (MCLCV), especially in Guatemala, in 2014 an extensive germplasm screen was organized to try to identify material that was resistant, or at least less susceptible. The screen for potentially resistant material was done through an open-field bio-assay. Since until now the virus cannot be mechanically transmitted, the success of the trial relied on the natural occurrence of the whiteflies, which are the vectors, and the virus itself. No resistant material was known at the time the bio-assay was planned, so it was not possible to include resistant controls. Susceptible controls were however easy to include; the commonly used variety Vedrantais was included as a general susceptible control, and the commercial hybrid variety Caribbean Gold F1 was also included, as it was observed to be susceptible as well. To determine if perhaps resistance was already present in cultivated material, a number of commercially available hybrid melon varieties from which the phenotype was not yet clear was also included.

For most accessions 20 seeds were sown in trays, so that at least 10 plants could be included in the field test. Seedlings were transplanted to the field after 2 weeks. Symptom observation according to the scales described in FIG. 3 was done after 58 days. Because fruit development was well on its way, all symptoms, and especially fruit cracking, could be very well observed.

All commercial hybrids that were included in the test were susceptible. This means that all of them had the typical MCLCV curling and yellowing symptoms, but also fruit cracking, which is the most devastating aspect of MCLCV, since fruits are obviously unmarketable when cracked. It was further found that almost all genebank accessions, including non-cultivated material, that were included in the test were susceptible as well. Fortunately, some material showed a certain level of resistance, and two were selected as the most interesting accessions, internal genebank numbers GBN.08.32 and GBN11251. Both were non-cultivated *C. melo* types that were categorized as *C. melo* subsp. *agrestis*, and had a number of plants with a high level of resistance.

Even though the presence of the fruit cracking symptoms made it clear symptoms were caused by MCLCV, to confirm the presence of MCLCV, plants with and without symptoms were tested with PCR, using the primers and PCR programme as described in Deng et al., 1994. The presence of MCLCV in the trial was positively confirmed through this test. From GBN.08.32, two selections derived from different plants of the original material were included in the test. One of the selections was derived from plant 27 (GBN.08.32-27), and of the 10 included plants, 9 were confirmed to be resistant through the qPCR test. From the other selection, derived from original plant 63, 11 plants were included in the trial, but only 3 were confirmed to be resistant through the qPCR test. Of the 9 plants included for GBN11251, 8 were confirmed to be resistant through the qPCR test. These results showed that the resistance was not uniformly present in the original non-cultivated accessions, and a program for selection would have to be started.

Example 2: Development of SSD Lines and Phenotyping of Resistance

Resistant plants of GBN.08.32 and GBN11251 that were identified as described in Example 1 were crossed with the susceptible cultivar Vedrantais. From GBN.08.32, it was decided to use only plants from the GBN.08.32-27 line. Subsequently, Single Seed Descent (SSD) lines were developed for each population. When F5 SSD populations were reached, a new field assay in Guatemala was organized to observe the MCLCV resistance of these F5 SSD lines. From each source, 120 F5 SSD lines were included in the test, with 20 plants per line in 2 repetitions (2×10 plants). The parents of the SSD populations, GBN.08.32-27, GBN11251, and Vedrantais were also included in the trial.

First a catch-row of susceptible material was sown in trays, and after 2 weeks these plants were transplanted to the field and covered. The plants of the catch-row were placed at the sides of the field, and at the beginning and end of each row. At that moment also the seeds for the actual test were sown. These were transplanted to the field, and covered, after 2 weeks. The plants were planted in two repetitions, to minimize the environmental variation. At that same time, the plants of the catch-row were uncovered. After 2 more weeks the plants of the test were uncovered, and from that time the disease started to spread. Four weeks after uncovering the test plants, they were ready for evaluation. Scoring was done according to the scale presented in FIG. 3. All of the plants of the susceptible catch-rows had a score 4 at the moment of evaluation.

From the 120 F5 SSD lines developed from the GBN.08.32-27 x Vedrantais population, 18 were observed to have a strong phenotypic resistance level. From the 120 F5 SSD lines developed from the GBN11251 x Vedrantais population, 25 were observed to have a strong phenotypic resistance level. The lines with strong phenotypic resistance had no fruit cracking, and an average score of 2.0 or lower according to the scale of FIG. 3. FIG. 4 shows the scores of a number of the observed SSD lines, the susceptible controls Caribbean Gold and Vedrantais, and the resistant parents.

Example 3: QTL Mapping and Marker Development

QTL mapping was done on F5 SSD lines developed from both populations (GBN.08.32-27 x Vedrantais) and (GBN.11251 x Vedrantais). For the (GBN.08.32-27 x Vedrantais) population 114 lines were included in the QTL mapping. For the (GBN.11251 x Vedrantais) population 107 lines were included. A total of 911 markers were available for the mapping, of which 419 and 445 were informative for each population respectively.

The first QTL mapping resulted in the identification of 3 QTLs contributing to MCLCV resistance, which each had a LOD score higher than 3.0. A first QTL contributing to MCLCV resistance was found on chromosome 2, spanning a region of around 27 cM. A second QTL for MCLCV resistance was identified on chromosome 11, spanning a region of around 22 cM. A third QTL was mapped to chromosome 6, spanning a region of around 11 cM.

After this first analysis, further finemapping was performed to further define the involved QTL regions, and to identify additional linked markers within the QTL regions. The regions and markers identified in this way, after finemapping, can be found in FIG. 5. SEQ ID NOs: 1 and 5 are flanking the QTL region on chromosome 11. SEQ ID NOs: 6 and 12 are flanking the QTL region on chromosome 2. SEQ ID NOs: 13 and 16 are flanking the QTL region on chromosome 6. The flanking markers as well as the other markers in the QTL regions could be used for identification of the presence of the QTL it represented. The flanking markers, as well as the markers between them, were all polymorphic between the resistant sources and susceptible material, such as Vedrantais.

Example 4: Analysis of the QTL Contribution to the MCLCV Resistance

Various recombinant lines with different QTL combinations were developed to observe their contribution to the MCLCV resistance. It was found that a combination of the QTLs of chromosome 2 and 11 did have a good effect on the reduction of the virus symptoms, and the combination led to resistant plants with an average score that was lower than 2.0. However, when qPCR was done on this material to determine the actual presence of the virus in these plants, it showed that the amount of virus was higher than in the resistant source. This indicated that the QTLs on chromosome 2 and 11 contributed to symptom reduction, but not to the reduction of virus titer.

Further qPCR studies showed that when a combination of the QTL on chromosome 11 with the QTL on chromosome 6 was made, the virus titer in the plants was reduced when compared to lines that did not have the QTL on chromosome 6. It was therefore concluded that the QTLs of chromosomes 2 and 11 contributed to at least MCLCV symptom reduction, and at least the QTL on chromosome 6 played a role in virus titer reduction. qPCR values of the resistant and susceptible lines are presented in FIG. 6; a lower value means a higher virus titer level in the plant.

Example 5: Additional Marker Development in the QTL Regions

To better define the location of the QTLs, and to be able to identify the presence of the MCLCV resistance even better, the QTL region was further examined and an additional analysis of the QTL regions was performed. It is advantageous to work with more markers in the QTL regions, because the additional markers help in defining the actual location of the resistance.

Populations were developed wherein the QTLs were introgressed in various backgrounds, and F2 plants comprising recombinations within the QTL of chromosome 11 were observed. Through segregation, the F2 populations had different combinations of one or more of the resistant QTLs, and each plant was screened for resistance. Subsequently the plants were genotyped with the markers that were identified earlier. In addition, other polymorphisms between resistant and susceptible plants in the QTL regions were identified, so they could be used as markers to identify the presence of the resistance.

FIG. 7 shows these additional markers for identification of the presence of the QTL regions on chromosomes 11, 2 and 6. Details on their location and which nucleotide is linked to the presence of the QTL, and thereby of resistance, are presented in FIG. 7.

The invention is further described by the following numbered paragraphs:

1. A cultivated *Cucumis melo* plant comprising a QTL on chromosome 11 which is located between SEQ ID NO:

1 and SEQ ID NO: 5, and/or a QTL on chromosome 2 which is located between SEQ ID NO: 6 and SEQ ID NO: 12, and/or a QTL on chromosome 6 which is located between SEQ ID NO: 13 and SEQ ID NO: 16, which QTLs confer resistance to Melon chlorotic leaf curl virus (MCLCV).

2. A cultivated *Cucumis melo* plant of paragraph 1, wherein the presence of the QTL on chromosome 11 is genetically linked to a marker chosen from the group comprising the SNPs as presented in any one of SEQ ID NOs: 1, 5, and 2 to 4, and 17 to 21; the presence of the QTL on chromosome 2 is genetically linked to a marker chosen from the group comprising the SNPs as presented in any one of SEQ ID NOs: 6, 12, and 7 to 11, and 22 to 27; and the presence of the QTL on chromosome 6 is genetically linked to a marker chosen from the group comprising the SNPs as presented in any one of SEQ ID NOs: 13, 16, and 14 and 15, and 28 to 36.

3. A cultivated *Cucumis melo* plant of paragraph 1 or 2, wherein the QTL is as comprised in the genome of a *Cucumis melo* plant representative seed of which was deposited with the NCIMB under deposit number NCIMB 43711, NCIMB 43712, NCIMB 43713, or NCIMB 43951.

4. A cultivated *Cucumis melo* plant of any of the paragraphs 1 to 3, wherein the QTL is introgressed from NCIMB 43711, NCIMB 43712, NCIMB 43713, or NCIMB 43951, or from a progeny plant thereof that has retained a QTL as defined in any one of those paragraphs.

5. A cultivated *Cucumis melo* plant of any of the paragraphs 1 to 4, which plant comprises a QTL on chromosome 11 and chromosome 2, or a QTL on chromosome 11 and chromosome 6, or a QTL on chromosome 2 and chromosome 6, or a QTL on chromosome 11 and chromosome 2 and chromosome 6.

6. A cultivated *Cucumis melo* plant of any of the paragraphs 1 to 5, wherein the QTL is homozygously present.

7. A cell of a cultivated *Cucumis melo* plant of any of the paragraphs 1 to 6, which cell comprises the QTL as defined in any of the paragraphs 1 to 4 on chromosome 11, and/or the QTL as defined in any of the paragraphs 1~4 on chromosome 2, and/or the QTL as defined in any of the paragraphs 1 to 4 on chromosome 6 in its genome.

8. A *Cucumis melo* seed comprising the QTL on chromosome 11 as defined in any of the paragraphs 1-4, and/or the QTL on chromosome 2 as defined in any of the paragraphs 1 to 4, and/or the QTL on chromosome 6 as defined in any of the paragraphs 1 to 4 in its genome, wherein a plant grown from the seed is a plant of any of the paragraphs 1 to 6.

9. Propagation material suitable for producing a *Cucumis melo* plant of any one of the paragraphs 1 to 6, wherein the propagation material is suitable for sexual reproduction, and is in particular selected from the group comprising a microspore, pollen, an ovary, an ovule, an embryo sac, and an egg cell; or is suitable for vegetative reproduction, and is in particular selected from the group comprising a cutting, a root, a stem, a cell, and a protoplast; or is suitable for tissue culture of regenerable cells, and is in particular selected from the group comprising a leaf, pollen, an embryo, a cotyledon, a hypocotyl, a meristematic cell, a root, a root tip, an anther, a flower, a seed, and a stem; wherein the plant produced from the propagation material comprises a QTL that leads to MCLCV resistance on chromosome 11, and/or on chromosome 2, and/or on chromosome 6, as defined in any of the paragraphs 1 to 4.

10. Marker for the identification of MCLCV resistance in a cultivated or non-cultivated *Cucumis melo* plant, which marker is any one of a group comprising the SNPs presented in SEQ ID NOs: 1, 5, and 2 to 4, and 17 to 21, for the identification of the QTL on chromosome 11; or any one of a group comprising the SNPs presented in SEQ ID NOs: 6, 12, and 7 to 11, and 22 to 27, for the identification of the QTL on chromosome 2; or any one of a group comprising the SNPs presented in SEQ ID NOs: 13, 16, and 14 and 15, and 28 to 36, for the identification of the QTL on chromosome 6.

11. Use of a marker of paragraph 10 for identification of MCLCV resistance in a *Cucumis melo* plant.

12. Method for producing a MCLCV resistant cultivated *Cucumis melo* plant comprising introgressing a QTL on chromosome 11 as defined in any of the paragraphs 1-4, and/or introgressing a QTL on chromosome 2 as defined in any of the paragraphs 1-4, and/or introgressing a QTL on chromosome 6 as defined in any of the paragraphs 1-4 into a cultivated *C. melo* plant.

13. Method for selecting a MCLCV resistant *Cucumis melo* plant, comprising identifying the presence of a QTL on chromosome 11, and/or on chromosome 2, and/or on chromosome 6 as defined in any of the paragraphs 1-4, and selecting a plant that comprises said QTL or combination of QTLs as a MCLCV resistant plant.

14. Method of paragraph 13 wherein identifying the presence of the QTL is done using a marker of any one of a group comprising the SNPs presented in SEQ ID NOs: 1, 5, and 2 to 4, and 17 to 21, for the identification of the QTL on chromosome 11; or any one of a group comprising the SNPs presented in SEQ ID NOs: 6, 12, and 7 to 11, and 22 to 27, for the identification of the QTL on chromosome 2; or any one of a group comprising the SNPs presented in SEQ ID NOs: 13, 16, and 14 to 15, and 28 to 26, for the identification of the QTL on chromosome 6.

15. A method for the production of a *Cucumis melo* plant, which is resistant to MCLCV, said method comprising:

a) crossing a plant of any one of the paragraphs 1-6 with another plant to obtain a first generation population;

b) optionally performing one or more rounds of selfing and/or crossing of the plant resulting from the cross to obtain a further generation population;

c) selecting from the plants resulting from the cross of step a), or from the further generation population of step b), a plant that comprises a QTL on chromosome 11, and/or a QTL on chromosome 2, and/or a QTL on chromosome 6 as defined in any of paragraphs 1-4, which plant is resistant to MCLCV.

16. Method of paragraph 15, wherein selection of a plant comprising a QTL on chromosome 11, and/or a QTL on chromosome 2, and/or a QTL on chromosome 6 is done by using a molecular marker genetically linked to the QTL, which is done using a marker of any one of a group comprising the SNPs presented in SEQ ID NOs: 1, 5, and 2 to 4, and 17 to 21, for the identification of the QTL on chromosome 11; or any one of a group comprising the SNPs presented in SEQ ID NOs: 6, 12, and 7 to 11, and 22 to 27, for the identification of the QTL on chromosome 2; or any one of a group comprising the SNPs presented in SEQ ID NOs: 13, 16, and 14 to 15, and 28 to 36, for the identification of the QTL on chromosome 6.

17. Method of paragraph 15, wherein a plant which is resistant to MCLCV is phenotypically selected, in particular by using a bio-assay for MCLCV resistance.

18. Method of any of the paragraphs 15-17, wherein the plant of any of the paragraphs 1-6 is a plant grown from seed deposited under NCIMB accession number NCIMB 43711, NCIMB 43712, NCIMB 43713, or NCIMB 43951, or a progeny plant thereof that has retained a QTL on chromosome 11, and/or on chromosome 2, and/or on chromosome 6.

19. Method for the production of cultivated hybrid *Cucumis melo* seed comprising crossing a first parent plant with a second parent plant and harvesting the resultant hybrid seed, wherein the first parent plant and/or the second parent plant is a plant of the invention comprising a QTL on chromosome 11, and/or on chromosome 2, and/or on chromosome 6 as defined in any of the paragraphs 1-4, wherein the presence of said QTL or combination of QTLs leads to resistance to MCLCV in the hybrid plant that is grown from the seed.

20. The cultivated hybrid *Cucumis melo* seed produced by the method of paragraph 19.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A cultivated *Cucumis melo* plant, wherein the genome of said cultivated *Cucumis melo* plant comprises:

a) a QTL on chromosome 11 which is located between SEQ ID NO: 1 and SEQ ID NO: 5 and a QTL on chromosome 2 which is located between SEQ ID NO: 6 and SEQ ID NO: 12; or b) the QTL on chromosome 11 and a QTL on chromosome 6 which is located between SEQ ID NO: 13 and SEQ ID NO: 16; or c) the QTL on chromosome 11, the QTL on chromosome 2, and the QTL on chromosome 6;

wherein presence of the QTL on chromosome 11 and the QTL on chromosome 2 as in a), the QTL on chromosome 11 and the QTL on chromosome 6 as in b); or the QTL on chromosome 11, the QTL on chromosome 2, and the QTL on chromosome 6 as in c) confers resistance to Melon chlorotic leaf curl virus (MCLCV) to the plant, wherein:

the QTL on chromosome 11 and the QTL on chromosome 2 as in a) is as comprised in the genome of a *Cucumis melo* plant, representative seed of which was deposited with the NCIMB under deposit number NCIMB 43712;

the QTL on chromosome 11 and the QTL on chromosome 6 as in b) is as comprised in the genome of a *Cucumis melo* plant, representative seed of which was deposited with the NCIMB under deposit number NCIMB 43951; and the QTL on chromosome 11, the QTL on chromosome 2, and the QTL on chromosome 6 as in c) is as comprised in the genome of a *Cucumis melo* plant, representative seed of which was deposited with the NCIMB under deposit number NCIMB 43713.

2. The cultivated *Cucumis melo* plant of claim 1, wherein:

the presence of the QTL on chromosome 11 is genetically linked to a marker, the marker comprising a SNP, the SNP comprising:

i) a C to A conversion at position 101 of SEQ ID NO: 1;

ii) a G to A conversion at position 101 of SEQ ID NO: 2;

iii) an A to G conversion at position 101 of SEQ ID NO: 3;

iv) an A to C conversion at position 101 of SEQ ID NO: 4;

v) a T to C conversion at position 101 of SEQ ID NO: 5;

vi) an A to C conversion at position 101 of SEQ ID NO: 17;

vii) a G to A conversion at position 101 of SEQ ID NO: 18;

viii) an A to G conversion at position 101 of SEQ ID NO: 19;

ix) a G to T conversion at position 101 of SEQ ID NO: 20; or x) a G to A conversion at position 101 of SEQ ID NO: 21;

relative to a wildtype genomic sequence of chromosome 11;

the presence of the QTL on chromosome 2 is genetically linked to a marker, the marker comprising a SNP, the SNP comprising:

xi) a C to T conversion at position 101 of SEQ ID NO: 6;

xii) an A to G conversion at position 101 of SEQ ID NO: 7;

xiii) an A to G conversion at position 101 of SEQ ID NO: 8;

xiv) an A to C conversion at position 101 of SEQ ID NO: 9;

XV) a T to C conversion at position 101 of SEQ ID NO: 10;

xvi) a C to A conversion at position 101 of SEQ ID NO: 11;

xvii) a G to A conversion at position 101 of SEQ ID NO: 12;

xviii) an A to G conversion at position 101 of SEQ ID NO: 22;

xix) a G to A conversion at position 101 of SEQ ID NO: 23;

xx) a T to A conversion at position 101 of SEQ ID NO: 24;

xxi) a G to T conversion at position 101 of SEQ ID NO: 25;

xxii) an A to G conversion at position 101 of SEQ ID NO: 26; or xxiii) a T to C conversion at position 101 of SEQ ID NO: 27;

relative to a wildtype genomic sequence of chromosome 2; and the presence of the QTL on chromosome 6 is genetically linked to a marker, the marker comprising a SNP, the SNP comprising:

xxiv) a T to C conversion at position 101 of SEQ ID NO: 13;

XXV) an A to C conversion at position 101 of SEQ ID NO: 14;

xxvi) a T to C conversion at position 101 of SEQ ID NO: 15;

xxvii) a C to A conversion at position 101 of SEQ ID NO: 16;

xxviii) an A to G conversion at position 101 of SEQ ID NO: 28;

xxix) a C to A conversion at position 101 of SEQ ID NO: 29;

XXX) an A to G conversion at position 101 of SEQ ID NO: 30;

xxxi) a C to T conversion at position 101 of SEQ ID NO: 31;

xxxii) a G to T conversion at position 101 of SEQ ID NO: 32;

xxxiii) a G to A conversion at position 101 of SEQ ID NO: 33;

xxxiv) an A to G conversion at position 101 of SEQ ID NO: 34;

XXXV) a C to G conversion at position 101 of SEQ ID NO: 35; or xxxvi) a T to A conversion at position 101 of SEQ ID NO: 36;

relative to a wildtype genomic sequence of chromosome 6.

3. The cultivated *Cucumis melo* plant of claim 1, wherein:

the QTL on chromosome 11 and the QTL on chromosome 2 as in a) is introgressed from NCIMB 43712;

the QTL on chromosome 11 and the QTL on chromosome 6 as in b) is introgressed from NCIMB 43951; and the QTL on chromosome 11, the QTL on chromosome 2, and the QTL on chromosome 6 as in c) is introgressed from NCIMB 43713, or from a progeny plant thereof that has retained the QTL on chromosome 11 and the QTL on chromosome 2 as in a), the QTL on chromosome 11 and the QTL on chromosome 6 as in b), or the QTL on chromosome 11, the QTL on chromosome 2, and the QTL on chromosome 6 as in c) as defined in claim 1.

4. The cultivated *Cucumis melo* plant of claim 1, comprising:

the QTL on chromosome 11 and the QTL on chromosome 2.

5. The cultivated *Cucumis melo* plant of claim 1, wherein the QTL on chromosome 11 and the QTL on chromosome 2 as in a), the QTL on chromosome 11 and the QTL on chromosome 6 as in b), or the QTL on chromosome 11, the QTL on chromosome 2, and the QTL on chromosome 6 as in c) is homozygously present.

6. A cell of the cultivated *Cucumis melo* plant of claim 1, which cell comprises the QTL on chromosome 11 and the QTL on chromosome 2 as in a), the QTL on chromosome 11 and the QTL on chromosome 6 as in b), or the QTL on chromosome 11, the QTL on chromosome 2, and the QTL on chromosome 6 as in c) in its genome.

7. A seed of, or from, or that produces the *Cucumis melo* plant of claim 1 and comprises the QTL on chromosome 11 and the QTL on chromosome 2 as in a), the QTL on chromosome 11 and the QTL on chromosome 6 as in b), or the QTL on chromosome 11, the QTL on chromosome 2, and the QTL on chromosome 6 as in c).

8. Propagation material from or suitable for producing the *Cucumis melo* plant of claim 1, wherein the propagation material is suitable for sexual reproduction, and a microspore, pollen, ovary, ovule, embryo sac or an egg cell, or the propagation material is suitable for vegetative reproduction and comprises a cutting, root, stem cell, or a protoplast, or the propagation material is suitable for tissue culture of regenerable cells or protoplasts and comprises a leaf, pollen, embryo, cotyledon, hypocotyl, meristematic cell, root, root tip, anther, flower or a stem, and wherein the propagation material comprises the QTL on chromosome 11 and the QTL on chromosome 2 as in a), the QTL on chromosome 11 and the QTL on chromosome 6 as in b), or the QTL on chromosome 11, the QTL on chromosome 2, and the QTL on chromosome 6 as in c).

9. A method of producing a *Cucumis melo* plant exhibiting resistance to Melon chlorotic leaf curl virus (MCLCV) comprising introducing into the genome of the *Cucumis melo* plant:

a) a QTL on chromosome 11 which is located between SEQ ID NO: 1 and SEQ ID NO: 5 and a QTL on chromosome 2 which is located between SEQ ID NO: 6 and SEQ ID NO: 12; or b) the QTL on chromosome 11 and a QTL on chromosome 6 which is located between SEQ ID NO: 13 and SEQ ID NO: 16; or c) the QTL on chromosome 11, the QTL on chromosome 2, and the QTL on chromosome 6;

wherein the plant is resistant to MCLCV as a result of the presence of the QTL on chromosome 11 and the QTL on chromosome 2 as in a), the QTL on chromosome 11 and the QTL on chromosome 6 as in b); or the QTL on chromosome 11, the QTL on chromosome 2, and the QTL on chromosome 6 as in c), and wherein:

the QTL on chromosome 11 and the QTL on chromosome 2 as in a) is as comprised in the genome of a *Cucumis melo* plant, representative seed of which was deposited with the NCIMB under deposit number NCIMB 43712;

the QTL on chromosome 11 and the QTL on chromosome 6 as in b) is as comprised in the genome of a *Cucumis melo* plant, representative seed of which was deposited with the NCIMB under deposit number NCIMB 43951; and the QTL on chromosome 11, the QTL on chromosome 2, and the QTL on chromosome 6 as in c) is as comprised in the genome of a *Cucumis melo* plant, representative seed of which was deposited with the NCIMB under deposit number NCIMB 43713.

10. A method for producing a *Cucumis melo* plant, comprising the steps of:

(a) crossing a first *Cucumis melo* parent plant with a second *Cucumis melo* parent plant to obtain an F1 population;

wherein the first *Cucumis melo* parent plant comprises in its genome:

i) a QTL on chromosome 11 which is located between SEQ ID NO: 1 and SEQ ID NO: 5 and a QTL on chromosome 2 which is located between SEQ ID NO: 6 and SEQ ID NO: 12; or ii) the QTL on chromosome 11 and a QTL on chromosome 6 which is located between SEQ ID NO: 13 and SEQ ID NO: 16; or iii) the QTL on chromosome 11, the QTL on chromosome 2, and the QTL on chromosome 6;

wherein:

the QTL on chromosome 11 and the QTL on chromosome 2 as in i) is as comprised in the genome of a *Cucumis melo* plant, representative seed of which was deposited with the NCIMB under deposit number NCIMB 43712;

the QTL on chromosome 11 and the QTL on chromosome 6 as in ii) is as comprised in the genome of a *Cucumis melo* plant, representative seed of which was deposited with the NCIMB under deposit number NCIMB 43951; and the QTL on chromosome 11, the QTL on chromosome 2, and the QTL on chromosome 6 as in iii) is as comprised in the genome of a *Cucumis melo* plant, representative seed of which was deposited with the NCIMB under deposit number NCIMB 43713;

(b) optionally performing one or more rounds of selfing and/or crossing with a F1 *Cucumis melo* plant to obtain a further generation population;

(c) selecting from the population resulting from the cross of step (a) or from the further generation population of step (b), a *Cucumis melo* plant that comprises the QTL on chromosome 11 and the QTL on chromosome 2 as in i), the QTL on chromosome 11 and the QTL on chromosome 6 as in ii); or the QTL on chromosome 11, the QTL on chromosome 2, and the QTL on chromosome 6 as in iii);

wherein presence of the QTL on chromosome 11 and the QTL on chromosome 2 as in i), the QTL on chromosome 11 and the QTL on chromosome 6 as in ii); or the QTL on chromosome 11, the QTL on chromosome 2, and the QTL on chromosome 6 as in iii) confers resistance to Melon chlorotic leaf curl virus (MCLCV) to the *Cucumis melo* plant.

11. The method of claim 10, wherein selection of a plant comprising the QTL on chromosome 11 and the QTL on chromosome 2 as in i), the QTL on chromosome 11 and the QTL on chromosome 6 as in ii); or the QTL on chromosome 11, the QTL on chromosome 2, and the QTL on chromosome 6 as in iii) is with a molecular marker genetically linked to each of the QTL on chromosome 11, the QTL on chromosome 2, and the QTL on chromosome 6, wherein:

the molecular marker for identifying presence of the QTL on chromosome 11 comprises an SNP, the SNP comprising:

i) a C to A conversion at position 101 of SEQ ID NO: 1;
ii) a G to A conversion at position 101 of SEQ ID NO: 2;
iii) an A to G conversion at position 101 of SEQ ID NO: 3;
iv) an A to C conversion at position 101 of SEQ ID NO: 4;
v) a T to C conversion at position 101 of SEQ ID NO: 5;
vi) an A to C conversion at position 101 of SEQ ID NO: 17;
vii) a G to A conversion at position 101 of SEQ ID NO: 18;
viii) an A to G conversion at position 101 of SEQ ID NO: 19;
ix) a G to T conversion at position 101 of SEQ ID NO: 20; or
x) a G to A conversion at position 101 of SEQ ID NO: 21;

relative to a wildtype genomic sequence of chromosome 11;

the molecular marker for identifying presence of the QTL on chromosome 2 comprises an SNP, the SNP comprising:

xi) a C to T conversion at position 101 of SEQ ID NO: 6;
xii) an A to G conversion at position 101 of SEQ ID NO: 7;
xiii) an A to G conversion at position 101 of SEQ ID NO: 8;
xiv) an A to C conversion at position 101 of SEQ ID NO: 9;
XV) a T to C conversion at position 101 of SEQ ID NO: 10;
xvi) a C to A conversion at position 101 of SEQ ID NO: 11;
xvii) a G to A conversion at position 101 of SEQ ID NO: 12;
xviii) an A to G conversion at position 101 of SEQ ID NO: 22;
xix) a G to A conversion at position 101 of SEQ ID NO: 23;
xx) a T to A conversion at position 101 of SEQ ID NO: 24;
xxi) a G to T conversion at position 101 of SEQ ID NO: 25;
xxii) an A to G conversion at position 101 of SEQ ID NO: 26; or
xxiii) a T to C conversion at position 101 of SEQ ID NO: 27;

relative to a wildtype genomic sequence of chromosome 2; and the molecular marker for identifying presence of the QTL on chromosome 6 comprises an SNP, the SNP comprising:

xxiv) a T to C conversion at position 101 of SEQ ID NO: 13;
XXV) an A to C conversion at position 101 of SEQ ID NO: 14;
xxvi) a T to C conversion at position 101 of SEQ ID NO: 15;
xxvii) a C to A conversion at position 101 of SEQ ID NO: 16;
xxviii) an A to G conversion at position 101 of SEQ ID NO: 28;
xxix) a C to A conversion at position 101 of SEQ ID NO: 29;
xxx) an A to G conversion at position 101 of SEQ ID NO: 30;
xxxi) a C to T conversion at position 101 of SEQ ID NO: 31;
xxxii) a G to T conversion at position 101 of SEQ ID NO: 32;
xxxiii) a G to A conversion at position 101 of SEQ ID NO: 33;
xxxiv) an A to G conversion at position 101 of SEQ ID NO: 34;
XXXV) a C to G conversion at position 101 of SEQ ID NO: 35; or
xxxvi) a T to A conversion at position 101 of SEQ ID NO: 36;

relative to a wildtype genomic sequence of chromosome 6.

12. The method of claim 10, wherein a plant which is resistant to MCLCV is phenotypically selected by using a bio-assay for MCLCV resistance.

13. The method of claim 10, wherein the first *Cucumis melo* parent plant is grown from a seed deposited under NCIMB accession number NCIMB 43712, NCIMB 43713, or NCIMB 43951, or a progeny plant thereof that has retained the QTL on chromosome 11 and the QTL on chromosome 2 as in i), the QTL on chromosome 11 and the QTL on chromosome 6 as in ii); or the QTL on chromosome 11, the QTL on chromosome 2, and the QTL on chromosome 6 as in iii).

14. A method for the production of cultivated hybrid *Cucumis melo* seed comprising:

crossing a first *Cucumis melo* parent plant with a second *Cucumis melo* parent plant, and harvesting the hybrid seed, wherein both *Cucumis melo* parent plants comprise in their respective genomes:

a) a QTL on chromosome 11 which is located between SEQ ID NO: 1 and SEQ ID NO: 5 and a QTL on chromosome 2 which is located between SEQ ID NO: 6 and SEQ ID NO: 12; or b) the QTL on chromosome 11 and a QTL on chromosome 6 which is located between SEQ ID NO: 13 and SEQ ID NO: 16; or c) the QTL on chromosome 11, the QTL on chromosome 2, and the QTL on chromosome 6;

wherein:

the QTL on chromosome 11 and the QTL on chromosome 2 as in a) is as comprised in the genome of a *Cucumis melo* plant, representative seed of which was deposited with the NCIMB under deposit number NCIMB 43712;

the QTL on chromosome 11 and the QTL on chromosome 6 as in b) is as comprised in the genome of a *Cucumis melo* plant, representative seed of which was deposited with the NCIMB under deposit number NCIMB 43951; and the QTL on chromosome 11, the QTL on chromosome 2, and the QTL on chromosome 6 as in c) is as comprised in the genome of a *Cucumis melo* plant, representative seed of which was deposited with the NCIMB under deposit number NCIMB 43713;

wherein the presence of the QTL on chromosome 11 and the QTL on chromosome 2 as in a), the QTL on chromosome 11 and the QTL on chromosome 6 as in b); or the QTL on chromosome 11, the QTL on chromosome 2, and the QTL on chromosome 6 as in c) leads to resistance to MCLCV in a hybrid plant that is grown from the seed.

15. A cultivated hybrid *Cucumis melo* seed produced by the method of claim 14, wherein the cultivated hybrid *Cucumis melo* seed comprises the QTL of a), or b) or c).

16. The cultivated *Cucumis melo* plant of claim 1, wherein the QTL on chromosome 11 and the QTL on chromosome 2 as in a), the QTL on chromosome 11 and the QTL on chromosome 6 as in b); or the QTL on chromosome 11, the QTL on chromosome 2, and the QTL on chromosome 6 as in c) is heterozygously present.

17. The cultivated *Cucumis melo* plant of claim 1, comprising the QTL on chromosome 11 and the QTL on chromosome 6.

18. The cultivated *Cucumis melo* plant of claim 1, comprising the QTL on chromosome 11, the QTL on chromosome 2, and the QTL on chromosome 6.

19. The method of claim 14, wherein the *Cucumis melo* parent plants comprise the QTL on chromosome 11 and the QTL on chromosome 6.

20. The method of claim 14, wherein the *Cucumis melo* parent plants comprise the QTL on chromosome 11, the QTL on chromosome 2, and the QTL on chromosome 6.

* * * * *